United States Patent
Guenther et al.

(10) Patent No.: US 9,764,505 B2
(45) Date of Patent: Sep. 19, 2017

(54) DEVICES AND METHODS FOR PRODUCING PLANAR POLYMERIC MATERIALS USING MICROFLUIDICS

(71) Applicant: The Governing Council of the University of Toronto, Toronto (CA)

(72) Inventors: Axel Guenther, Toronto (CA); Lian Leng, LaSalle (CA); Andrew Wollard, Toronto (CA); Arianna McAllister, Toronto (CA); Milica Radisic, Toronto (CA); Boyang Zhang, Toronto (CA)

(73) Assignee: THE GOVERNING COUNCIL OF THE UNIVERSITY OF TORONTO, Toronto, ON (CA)

( * ) Notice: Subject to any disclaimer, the term of this patent is extended or adjusted under 35 U.S.C. 154(b) by 439 days.

(21) Appl. No.: 14/360,546

(22) PCT Filed: Nov. 23, 2012

(86) PCT No.: PCT/CA2012/050847
§ 371 (c)(1),
(2) Date: May 23, 2014

(87) PCT Pub. No.: WO2013/075248
PCT Pub. Date: May 30, 2013

(65) Prior Publication Data
US 2014/0306371 A1    Oct. 16, 2014

Related U.S. Application Data

(60) Provisional application No. 61/623,445, filed on Apr. 12, 2012, provisional application No. 61/563,506, filed on Nov. 23, 2011.

(51) Int. Cl.
*B29C 47/00* (2006.01)
*C12M 3/06* (2006.01)
(Continued)

(52) U.S. Cl.
CPC ........ *B29C 47/0021* (2013.01); *A23G 3/0002* (2013.01); *C12M 23/16* (2013.01); *B01L 3/5027* (2013.01)

(58) Field of Classification Search
CPC .......................... B29C 47/0021; A23G 3/0002
(Continued)

(56) References Cited

U.S. PATENT DOCUMENTS 5,976,630 A    11/1999   Korokeyi et al.
6,149,072 A    11/2000   Tseng
(Continued)

FOREIGN PATENT DOCUMENTS

CA        2772050 A1       7/2004
WO    2010/027812 A2       3/2010
(Continued)

OTHER PUBLICATIONS

Chan et al., "Three-dimensional Photopatterning of Hydrogels Using Stereolithography for Long-term Cell Encapsulation", Lab Chip, vol. 10, The Royal Society of Chemistry, 2010, pp. 2062-2070.
(Continued)

*Primary Examiner* — Nahida Sultana
(74) *Attorney, Agent, or Firm* — Hill & Schumacher

(57) ABSTRACT

Methods and devices are disclosed for providing the controlled formation of planar homogeneous or heterogeneous materials using microfluidic devices. In one embodiment, a planar array of microfluidic channels is employed to produce a flowing liquid sheet having heterogeneous structure by spatially and temporally controlling dispensing of polymer liquid from selected microchannels. The resulting liquid sheet is solidified to produce a planar heterogeneous material that may be continuously drawn and/or fed from the plurality of microfluidic channels. The polymer liquid may
(Continued)

include a payload that may be selectively incorporated into the heterogeneous structure. In some embodiments, the local material composition is controllable, thereby allowing control over local and bulk material properties, such as the permeability and the elasticity, and of creating materials with directionally dependent properties.

28 Claims, 24 Drawing Sheets

(51) Int. Cl.
 *A23G 3/34* (2006.01)
 *B01L 3/00* (2006.01)

(58) Field of Classification Search
 USPC .................................. 264/177.18; 425/67
 See application file for complete search history.

(56) References Cited

U.S. PATENT DOCUMENTS

| | | | |
|---|---|---|---|
| 6,787,088 B2* | 9/2004 | Parce | B01J 19/0093 137/833 |
| 8,007,746 B2* | 8/2011 | Unger | B01L 3/5025 422/547 |
| 8,273,245 B2* | 9/2012 | Jovanovic | B01D 61/18 210/321.71 |
| 8,790,874 B2* | 7/2014 | Guenther | G01N 33/5088 435/284.1 |
| 2007/0105972 A1 | 5/2007 | Doyle et al. | |
| 2009/0238908 A1* | 9/2009 | Korolainen | B29C 47/265 425/113 |
| 2010/0223175 A1* | 9/2010 | Miglis | G06Q 40/04 705/37 |
| 2011/0284110 A1* | 11/2011 | Gagnon | B01L 3/502707 137/597 |
| 2011/0287469 A1* | 11/2011 | Guenther | G01N 33/5088 435/29 |
| 2012/0083046 A1 | 4/2012 | Watson et al. | |
| 2012/0264134 A1 | 10/2012 | Ionescu-Zanetti et al. | |
| 2012/0270337 A1* | 10/2012 | Dendukuri | B01L 1/00 436/501 |
| 2012/0298037 A1* | 11/2012 | Paul | B01F 5/0475 118/712 |
| 2015/0253232 A1* | 9/2015 | Guenther | A61B 5/00 435/29 |
| 2016/0068385 A1* | 3/2016 | Chen | B81C 1/00119 435/309.1 |

FOREIGN PATENT DOCUMENTS

| | | |
|---|---|---|
| WO | 2011/080538 A1 | 7/2011 |
| WO | 2012/054195 A2 | 4/2012 |
| WO | 2012/155110 A1 | 11/2012 |
| WO | 2012/171983 A2 | 12/2012 |
| WO | 2013/040078 A2 | 3/2013 |
| WO | 2013/040087 A2 | 3/2013 |

OTHER PUBLICATIONS

Yeh et al., "Micromolding of Shape-Controlled, Harvestable Cell-Laden Hydrogels", Biomaterials, vol. 27, Science Direct, 2006, pp. 5391-5398.
Search Report received for European application 12851166.4, dated Jun. 29, 2015, 9 pages.
Tan et al., "Microscale Multilayer Cocultures for Biomimetic Blood Vessels", J. Biomed. Mater. Res., Part A 72A, 2005, pp. 146-160.
Unger et al., "Monolithic Microfabricated Valves and Pumps by Multilayer Soft Lithography", Science, vol. 288, No. 5463, Apr. 7, 2000, pp. 113-116.
Walther et al., "Janus Particles", Soft Matter, vol. 4, 2008, pp. 663-668.
Whitesides et al., "Self-Assembly at All Scales", Science, vol. 295, Mar. 29, 2002, pp. 2418-2421.
Young et al., "Matrix-Dependent Adhesion of Vascular and Valvular Endothelial Cells in Microfluidic Channels", Lab Chip, vol. 7, 2007, pp. 1759-1766.
International Search Report received for PCT Patent Application No. PCT/CA2012/050847, mailed on Mar. 13, 2013, 4 pages.
International Search Report received for PCT Patent Application No. PCT/CA2014/050413, mailed on Aug. 12, 2014, 4 pages.
Written Opinion received for PCT Patent Application No. PCT/CA2012/050847, mailed on Mar. 13, 2013, 4 pages.
Anna et al., "Formation of Dispersions using "Flow Focusing" in Microchannels", Applied Physics Letters, vol. 82, No. 364, Jan. 20, 2003, pp. 364-366.
Augst et al., "Alginate Hydrogels as Biomaterials", Macromolecular Bioscience, vol. 6, 2006, pp. 623-633.
Bong et al., "Hydrodynamic Focusing Lithography", Flow Lithography, Angewandte Chemie-International Edition, vol. 49, 2010, 12 pages.
Born et al., "Estimation of Disruption of Animal Cells by Laminar Shear Stress", Biotechnology and Bioengineering, vol. 40, 1992, pp. 1004-1010.
Bowden et al., "Self-Assembly of Mesoscale Objects into Ordered Two-Dimensional Arrays", Science, vol. 276, Apr. 11, 1997, pp. 233-235.
Brown et al., "Pulsatile Perfusion Bioreactor for Cardiac Tissue Engineering", Biotechnol. Prog., vol. 24, No. 4, 2008, pp. 907-920.
Bruzewicz et al., "Fabrication of a Modular Tissue Construct in a Microfluidic Chip", Lab Chip, vol. 8, 2008, pp. 663-671.
Carrier et al., "Perfusion Improves Tissue Architecture of Engineered Cardiac Muscle", Tissue Engineering, vol. 8, 2002, pp. 175-188.
Casey et al., "Hibernation in Noncontracting Mammalian Cardiomyocytes", Circulation, vol. 102, 2000, pp. 3124-3129.
Chapin et al., "High-Throughput Flow Alignment of Barcoded Hydrogel Microparticles", Lab Chip, vol. 9, 2009, pp. 3100-3109.
Chen et al., "Janus Particles Templated from Double Emulsion Droplets Generated Using Microfluidics", Langmuir, vol. 25, No. 8, 2009, pp. 4320-4323.
Cho et al., "High-Throughput Optofluidic Platforms for Mosaicked Microfibers toward Multiplex Analysis of Biomolecules", Lab Chip, vol. 12, 2012, pp. 3676-3679.
Choi et al., "Microfluidic Fabrication of Complex-Shaped Microfibers by Liquid Template-Aided Multiphase Microflow", Lab Chip, vol. 11, 2011, pp. 1477-1483.
Choi et al., "Microfluidic Scaffolds for Tissue Engineering", Nature Materials, vol. 6, Nov. 2007, pp. 908-915.
Chung et al., "Guided and Fluidic Self-Assembly of Microstructures Using Railed Microfluidic Channels", Nature Materials, vol. 7, Jul. 2008, pp. 581-587.
Davies, Peter F., "Flow-Mediated Endothelial Mechanotransduction", Physiological Reviews, vol. 75, No. 3, Jul. 1995, pp. 1-75.
Dendukuri et al., "Continuous-Flow Lithography for High-Throughput Microparticle Synthesis", Nature Materials, vol. 5, May 2006, pp. 365-369.
Derda et al., "Multizone Paper Platform for 3D Cell Cultures", PLoS One, vol. 6, No. 5, May 2011, 14 pages.
Dewey et al., "The Dynamic Response of Vascular Endothelial Cells to Fluid Shear Stress", Journal of Biomechanical Engineering, vol. 103, Aug. 1981, pp. 177-185.
Du et al., "Directed Assembly of Cell-Laden Microgels for Fabrication of 3D Tissue Constructs", Proceedings of the National Academy of Sciences of the USA, vol. 105, No. 28, Jul. 15, 2008, pp. 9522-9527.
Fang et al., "Binding Behavior of Calcium to Polyuronates: Comparison of Pectin with Alginate", Carbohydrate Polymers, vol. 72, 2008, pp. 334-341.
Fernandez et al., "Micro-Masonry: Construction of 3D Structures by Microscale Self-Assembly", Advanced Materials, vol. 22, 2010, pp. 1-4.

(56) References Cited

OTHER PUBLICATIONS

Glotzer et al., "Anisotropy of Building Blocks and Their Assembly into Complex Structures", Nature Materials, vol. 6, Aug. 2007, pp. 557-562.
Iyer et al., "Spatiotemporal Tracking of Cells in Tissue Engineered Cardiac Organoids", Journal of Tissue Engineering and Regenerative Medicine, vol. 3, 2009, pp. 196-207.
Kachouie et al.", Directed Assembly of Cell-Laden Hydrogels for Engineering Functional Tissues", Organogenesis, vol. 6, No. 4, 2010, pp. 234-244.
Kang et al., "Digitally Tunable Physicochemical Coding of Material Composition and Topography in Continuous Microfibres", Nature Materials, vol. 10, 2011, pp. 877-883.
Kim et al., "Synthesis of Nonspherical Colloidal Particles with Anisotropic Properties", Journal of the American Chemical Society, vol. 128, 2006, pp. 14374-14377.
Knight et al., "Hydrodynamic Focusing on a Silicon Chip: Mixing Nanoliters in Microseconds", Physical Review Letters, vol. 80, No. 17, Apr. 27, 1998, pp. 3863-3866.
Kuo et al., "Ionically Crosslinked Alginate Hydrogels as Scaffolds for Tissue Engineering: Part 1. Structure, Gelation Rate and Mechanical Properties", Biomaterials, vol. 22, 2001, pp. 511-521.
Ladet et al., "Multi-Membrane Hydrogels", Nature, vol. 452, Mar. 6, 2008, 5 pages.
Lee et al., "Colour-Barcoded Magnetic Microparticles for Multiplexed Bioassays", Nature Materials, vol. 9, Sep. 2010, pp. 745-749.
Lee et al., "On-Demand Three-Dimensional Freeform Fabrication of Multi-Layered Hydrogel Scaffold with Fluidic Channels", Biotechnology and Bioengineering, vol. 105, No. 6, Apr. 15, 2010, pp. 1178-1186.
Leng et al., "Flow-Based Organization of Soft Materials in 3D", American Physical Society, Annual Meeting of the APS Division of Fluid Dynamics, Mar. 18, 2009, 11 pages.
Leng, Lian, "Flow-Based Organization of Perfusable Soft Material in Three Dimensions", Graduate Department of Mechanical and Industrial Engineering University of Toronto, 2010, 92 pages.
Leng et al., "Massively Scaled Microfluidic Device for the Flow-Based Formation of 3D Perfusable Scaffold", American Institute of Chemical Engineers Annual Meeting, Nov. 11, 2009, 14 pages.
Li et al., "Culture of Neural Stem Cells in Calcium Alginate Beads", Biotechnology Progress, vol. 22, 2006, pp. 1683-1689.
Nagakura et al., "Effect of Viscous Injectable Pure Alginate Sol on Cultured Fibroblasts", Plastic and Reconstructive Surgery, vol. 116, 2005, pp. 831-838.
Nair et al., "Characterization of Cell Viability During Bioprinting Processes", Biotechnology Journal, vol. 4, 2009, pp. 1168-1177.
Naito et al., "Optimizing Engineered Heart Tissue for Therapeutic Applications as Surrogate Heart Muscle", Circulation, vol. 114, Jul. 4, 2006, pp. I72-I78.
Nie et al., "Janus and Ternary Particles Generated by Microfluidic Synthesis: Design, Synthesis, and Self-Assembly", Journal of the American Chemical Society, vol. 128, 2006, pp. 9408-9412.
Nunes et al., "Dripping and Jetting in Microfluidic Multiphase Flows Applied to Particle and Fibre Synthesis", Journal of Physics D: Applied Physics, vol. 46, Feb. 22, 2013, 20 pages.
Plouffe et al., "Controlled Capture and Release of Cardiac Fibroblasts using Peptide-Functionalized Alginate Gels in Microfluidic Channels", Lab Chip, vol. 9, 2009, pp. 1507-1510.
Pokrywczynska et al., "Alginate Is Not a Good Material for Growth of Rapidly Proliferating Cells", Transplantation Proceedings, vol. 40, 2008, pp. 1664-1667.
Pregibon et al., "Multifunctional Encoded Particles for High-Throughput Biomolecule Analysis", Science, vol. 315, 2007, pp. 1393-1396.
Qi et al., "Patterned Differentiation of Individual Embryoid Bodies in Spatially Organized 3D Hybrid Microgels", Advanced Materials, vol. 22, 2010, pp. 5276-5281.
Radisic et al., "Oxygen Gradients Correlate With Cell Density and Cell Viability in Engineered Cardiac Tissue", Biotechnology and Bioengineering, vol. 93, No. 2, Feb. 5, 2006, pp. 332-343.
Saunders et al., "Delivery of Human Fibroblast Cells by Piezoelectric Drop-On-Demand Inkjet Printing", Biomaterials, vol. 29, 2008, pp. 193-203.

\* cited by examiner

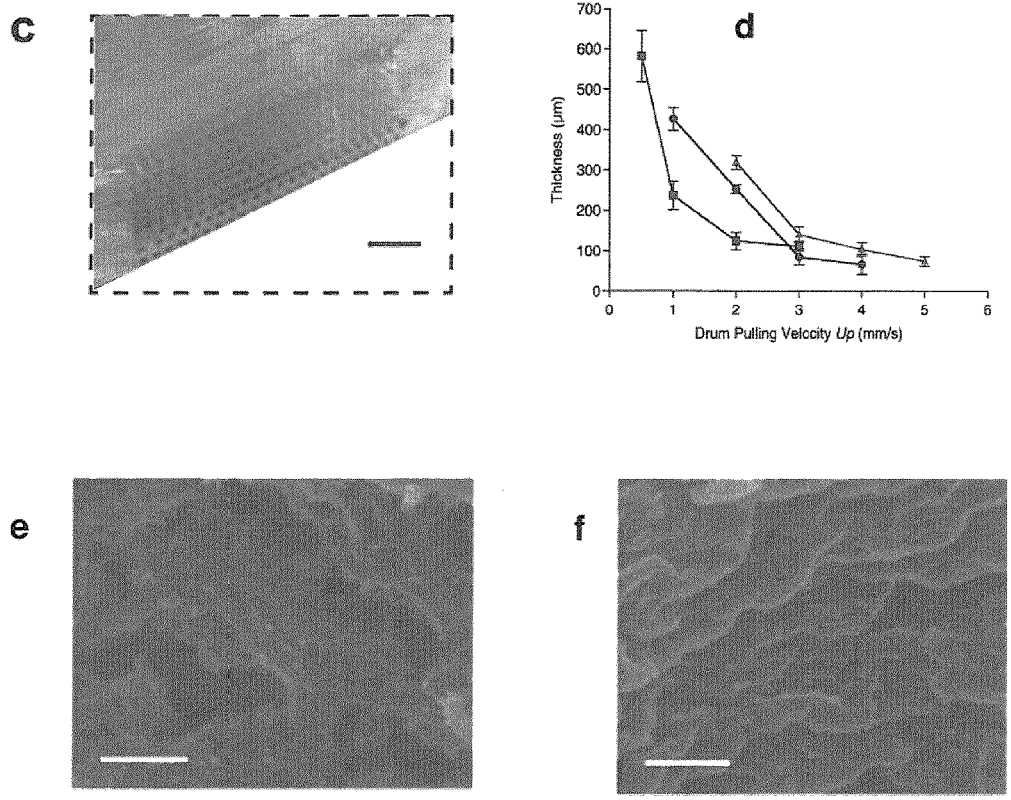
Figure 2 (Cont')

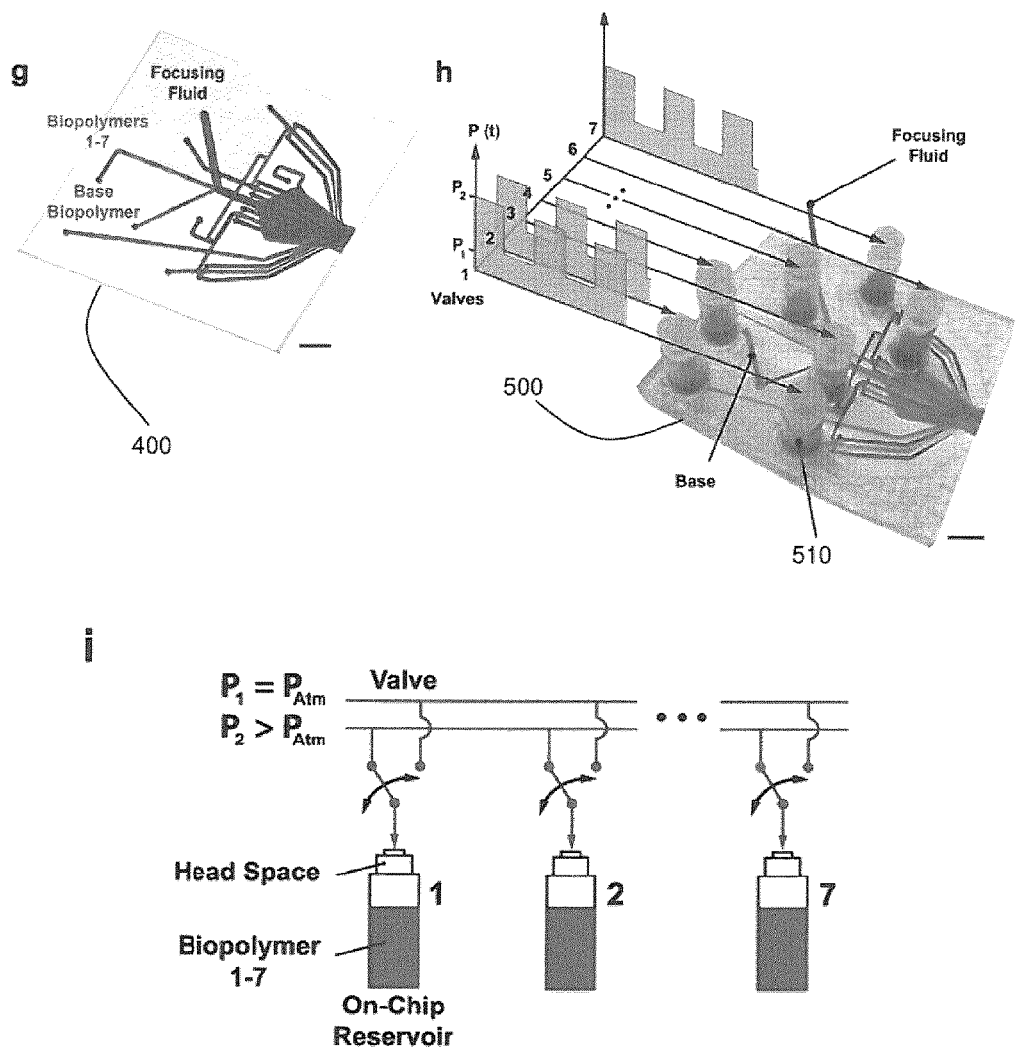
Figure 2 (Cont')

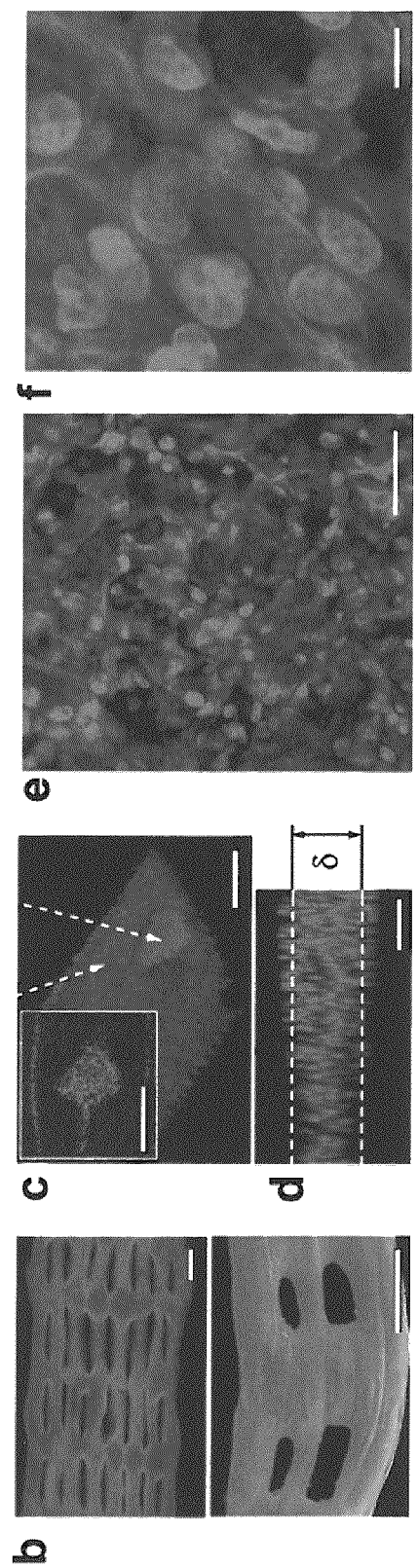
Figure 3 (Cont')

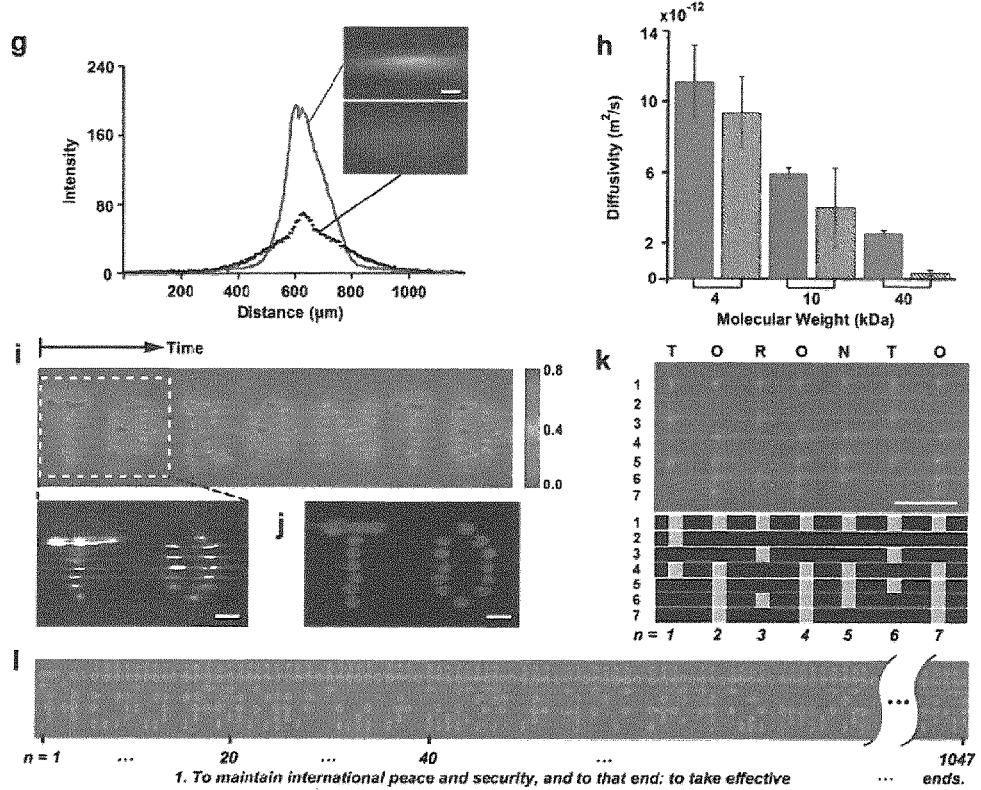
Figure 3 (Cont')

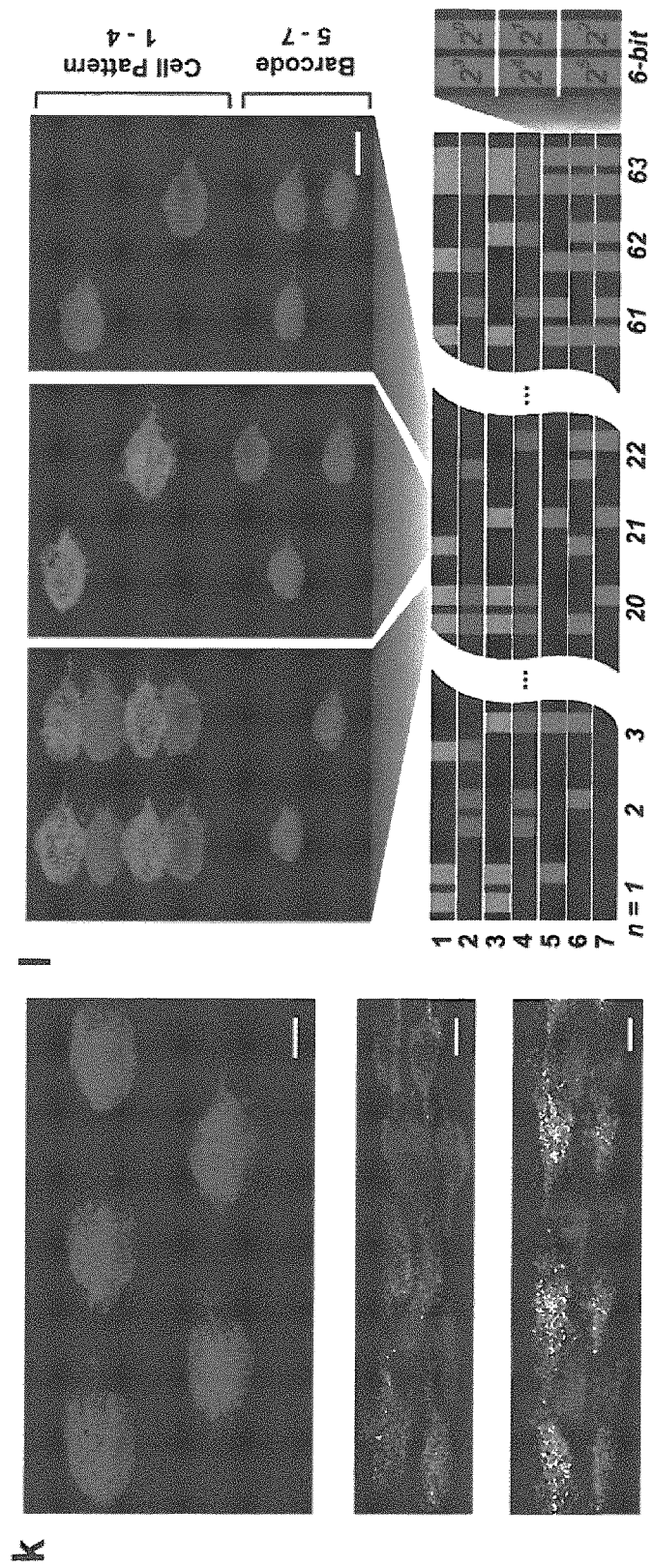
Figure 4 (Cont')

1. To maintain international peace and security, and to that end: to take effective collective measures for the prevention and removal of threats to the peace, and for the suppression of acts of aggression or other breaches of the peace, and to bring about by peaceful means, and in conformity with the principles of justice and international law, adjustment or settlement of international disputes or situations which might lead to a breach of the peace; 2. To develop friendly relations among nations based on respect for the principle of equal rights and self-determination of peoples, and to take appropriate measures to strengthen universal peace; 3. To achieve international co-operation in solving inter national problems of an economic, social, cultural, or humanitarian character, and in promoting and encouraging respect for human rights and for fundamental freedoms for all without distinction as to race, sex, language, or religion; and 4. To be a centre for harmonizing the actions of nations in the attainment of these common ends.

Figure 9

DEVICES AND METHODS FOR PRODUCING PLANAR POLYMERIC MATERIALS USING MICROFLUIDICS

CROSS-REFERENCE TO RELATED APPLICATION

This application is a National Phase application claiming the benefit of PCT/CA2012/050847 filed on Nov. 23, 2012, in English, which further claims priority to U.S. Provisional Application No. 61/563,506 titled "DEVICE AND METHODS FOR DIGITAL PRINTING" and filed on Nov. 23, 2011, the entire contents of which are incorporated herein by reference, and to U.S. Provisional Application No. 61/623,445 titled "DEVICES AND METHODS FOR PRODUCING CONTROLLED HETEROGENEITY IN PLANAR MATERIALS USING MICROFLUIDICS" and filed on Apr. 12, 2012, the entire contents of which are incorporated herein by reference.

BACKGROUND

The present disclosure relates to devices and methods for forming heterogeneous materials using microfluidics.

Materials with a spatially non-uniform composition that is closely linked to their function are common in nature and often possess a hierarchical architecture with length scales ranging from hundreds of nanometers to several millimeters. Currently available strategies for creating materials with an organized microscale composition mimic nature's ability in two ways: by initially preparing building blocks and subsequently assembling them along fluid interfaces and by replica molding. These strategies necessitate a sequence of processing steps and often lack spatiotemporal control. To date, the controlled formation of heterogeneous soft materials has been limited to particles (e.g., encapsulated and Janus particles) and coded fibers.

SUMMARY

Methods and devices are disclosed for providing the controlled formation of planar homogeneous or heterogeneous polymeric materials using microfluidic devices. In one embodiment, a planar array of microfluidic channels is employed to produce a flowing liquid sheet having heterogeneous structure by spatially and temporally controlling dispensing of polymer liquid from selected microchannels. The resulting liquid sheet is polymerized to produce a planar heterogeneous material that may be continuously drawn and/or fed from the plurality of microfluidic channels. The liquid may include a payload that may be selectively incorporated into the polymeric structure. In some embodiments, the local material composition is controllable, thereby allowing control over local and bulk material properties, such as the permeability and the elasticity, and of creating materials with directionally dependent properties.

Accordingly, in one aspect, there is provided a microfluidic device comprising:
a substantially planar array of microfluidic channels, wherein inlets of said microfluidic channels are connectable to one or more liquid polymer dispensing devices for delivering polymer solution at a controlled rate;
a substantially planar channel having:
an inlet in fluid communication with outlets of said microfluidic channels,
a length such that the polymer solution emerges from an outlet of the planar channel as a substantially planar liquid sheet; and
a polymerization reservoir in fluid communication with the outlet of the planar channel for receiving the planar liquid sheet into an additional liquid, such that the planar liquid sheet is polymerizable into a substantially planar polymeric material within the additional liquid.

In another embodiment, there is provided a method of forming a planar polymeric material using a microfluidic device, the microfluidic device comprising:
a substantially planar array of microfluidic channels, wherein inlets of said microfluidic channels are connected to one or more liquid polymer dispensing devices for delivering at least one polymer solution at a controlled rate;
a substantially planar channel having:
an inlet in fluid communication with outlets of said microfluidic channels,
a length such that the polymer solution emerges from an outlet of the planar channel as a substantially planar liquid sheet; and
a polymerization reservoir in fluid communication with the outlet of the planar channel, wherein the polymerization reservoir contains an additional liquid;
the method comprising:
controlling the one or more liquid polymer dispensing devices to dispense the polymer solution into the microfluidic channels at a controlled rate; and
polymerizing the planar liquid sheet as it emerges from the output of the planar channel into the additional liquid, thereby forming a substantially planar polymeric material.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 9 shows line camera intensity measurements of the UN Charter, Chapter 1, Article 1, "The purposes of the United Nations".

DETAILED DESCRIPTION

Figure 1:
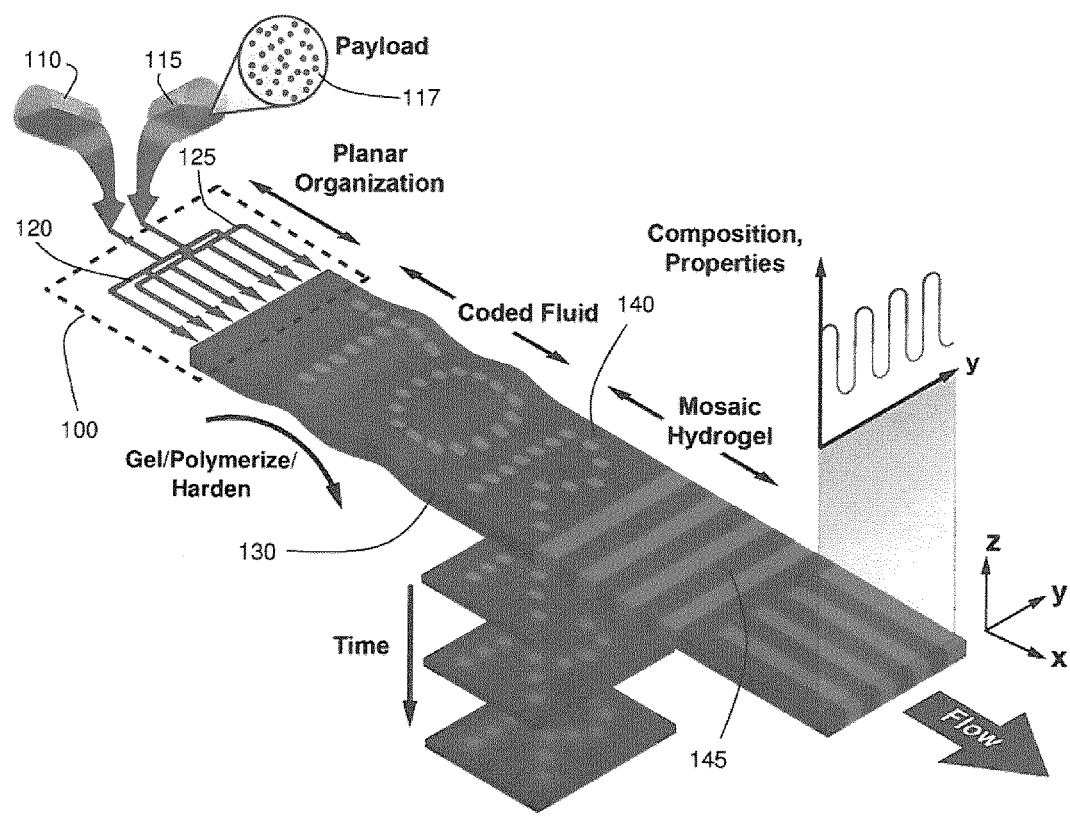
FIG. 1 schematically illustrates a method for the formation of a planar heterogeneous hydrogel using a flow-focusing microfluidic device.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the phrase "microfluidic" refers to a device, or a fluidic component of a device, that is configured for containing, flowing, processing, or otherwise manipulating of volumes of liquid in the sub-picoliter to sub-milliliter range. In some example embodiments, the maximal cross-sectional dimension of a microfluidic feature, such as a microfluidic channel, may be less than 1 mm, less than 500 microns, less than 100 microns, less than 50 microns, or less than 25 microns.

As used herein, the term "biopolymer" is understood to encompass naturally occurring polymers, as well as synthetic modifications or derivatives thereof. Such biopolymers include, without limitation, hyaluronic acid, collagen, recombinant collagen, cellulose, elastin, alginates, chondroitin sulfate, chitosan, chitin, keratin, silk, blends thereof as well as physical and chemical modifications of thereof.

As used herein, the phrase "polymer solution" refers to a solution containing a polymerizable substance. Similarly, the phrase "biopolymer solution" refers to a solution containing a substance that is polymerizable into a biopolymer.

Embodiments of the present disclosure provide a microfluidic approach for the controlled formation of planar polymeric materials. A planar array of microfluidic channels is employed to produce a flowing liquid sheet, which may be formed with a heterogeneous structure by spatially and temporally controlling dispensing of a polymer solution from the microchannels. The resulting liquid sheet is solidified to produce a planar heterogeneous material that may be continuously drawn and/or fed from the plurality of microfluidic channels. The ability to dynamically control the local material composition also provides an effective means of altering local and bulk material properties, such as the permeability and the elasticity, and of creating materials with directionally dependent properties.

FIG. 1 schematically illustrates an example microfluidic method for producing a planar heterogeneous material from two or more biopolymer solution sources. Microfluidic device (schematically shown at 100) dynamically incorporates at least one secondary biopolymer solution 115 within a layer 130 formed with base biopolymer solution 110, based on the controlled dispending of secondary biopolymer solution 115 from microfluidic channels. The base biopolymer solution 110 and secondary biopolymer solution 120 biopolymer solution solidify into a planar material of controlled heterogeneity upon exit of microfluidic device 100.

As will be further described below, base biopolymer solution 110 and secondary biopolymer solution 115 flow within microfluidic device 100 through base microfluidic array 120 and secondary microfluidic array 125 respectively, with the microfluidic channels of the arrays arranged such that near an output of microfluidic device 100, the outputs of the microfluidic channels forming secondary microfluidic array 125 (containing secondary biopolymer solution 115) are spatially interleaved with outputs of the microfluidic channels forming base microfluidic array 120 (containing base biopolymer solution 110), as shown in the Figure.

Figure 3A:
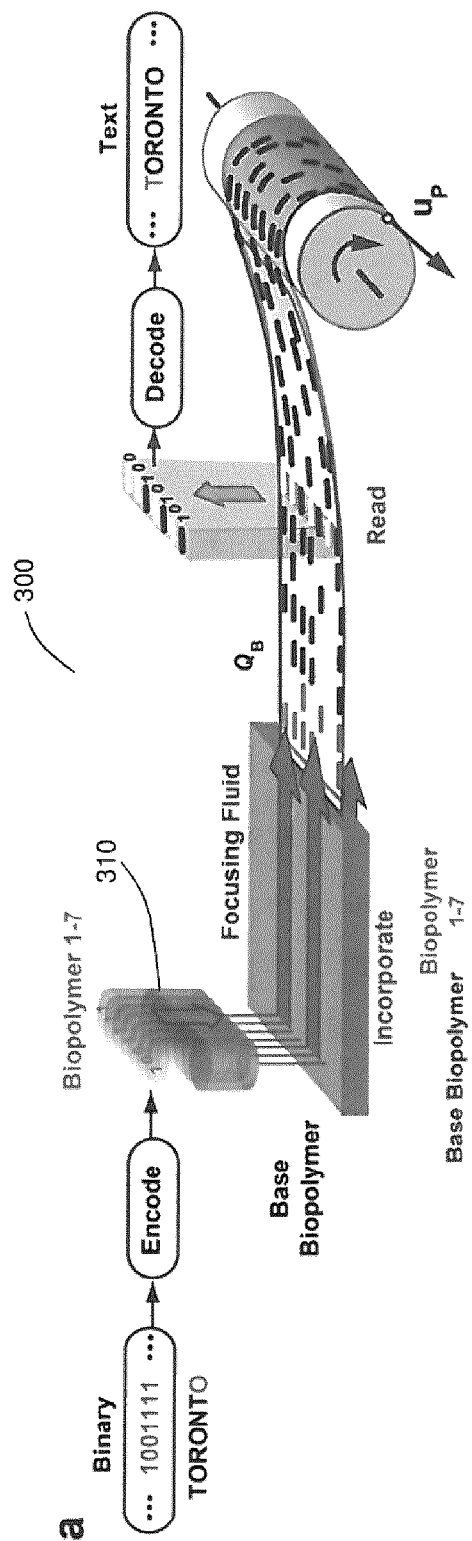
FIG. 3 demonstrates dynamically encoding spots and information in planar hydrogels, showing (a) an illustration of encoding information by dynamically incorporating spots of a secondary (fluorescently labeled) biopolymer into a base biopolymer and subsequently decoding the contained information; (b) a hydrogel sheet with an array of void areas as imaged by confocal fluorescence (top) and scanning electron microscopy (bottom); (c) confocal fluorescence image illustrating dimensions and shape of spots created by incorporating a secondary biopolymer with a payload of fluorescently labeled microspheres at conditions P=3.5 kPa, $Q_B$=160 µl/min, UP=12 mm/s, $t_v$=50 ms (insets represent the xy-plane (center location of sheet); d) confocal fluorescence image (x-z plane) of cardiomyocytes incorporated within a planar biomaterial (top and bottom sheet boundaries indicated by dashed lines); e) confocal fluorescence image of spot with incorporated fibroblasts at a cell density of 10 million cells/mL (40×, Day 5); f) 5× magnification confocal scan of fibroblasts spot shown in (e) (40×, Day 5); g) wide-field fluorescence image and corresponding distributions of 100 µM 40 kDa FITC-dextran loaded in 2% w.t. alginate and incorporated into the same base material (images captured at times 0 and 3 hrs.); h) diffusivity of 4 kDa, 10 kDa, and 40 kDa dextran in 2% w.t. alginate (dark gray), 1% w.t. pectin-1% w.t. alginate (light gray); i) line camera intensity scan (top) and fluorescence image (bottom) of encoded letters; j) fluorescence image of pattern formed with 10 million/mL cardiomyocytes in 1.2% w.t. alginate and in 0.08% w.t. collagen type I from rat tail (Day 0) (approximately 25,000 cells were incorporated, operating conditions: P=3.5 kPa, $Q_B$=160 µl/min, $U_P$=12 mm/s, valve 65 ms open; k) fluorescence line scan of binary code (top) and schematic of valve actuation with white sections corresponding to valve open (bottom) (n=7 binary characters); l) sample fluorescence line scan of the UN charter in ASCII code (n=1, 2, . . . 1047 binary characters including space); scale bars are 500 µm (b), 150 µm (c), 200 µm (d), 50 µm (e), 10 µm (f), 100 µm (g) and 2 mm (i-k).

In the present example embodiment, the dispensing of secondary biopolymer solution 115 from secondary microfluidic array 125 is controllable on a per-microfluidic channel basis by per-channel dispensing or metering mechanisms or devices (not shown in FIG. 1, but shown, for example, in FIG. 3a). Accordingly, the flow of secondary biopolymer solution 115 from a given microfluidic channel of secondary array 125 may be actuated on or off, thereby controlling the relative contribution of secondary biopolymer solution to the composition of the combined fluidic layer formed by the microfluidic channels in the array.

At the fluid exit of microfluidic device 100, the microfluidic array 120 and secondary microfluidic arrays 125 may be sandwiched between upper and lower planar flows of focusing fluid (not shown in FIG. 1, but shown, for example, in FIGS. 2 and 3) to focus the fluid layer formed by the biopolymer solution emerging from base 120 and secondary 125 microfluidic channels. Such a flow focusing embodiment enables the spatial localization of the fluid streams emerging from the microfluidic device, with the ability to spatially localize the fluid stream layer into a planar fluidic sheet having a thickness that is controllable (by controlling the flow rate and/or other properties of the flow focusing fluid) and may be substantially thinner than a thickness (or height) of the microfluidic channel apertures. Furthermore, the focusing fluid serves to confine the extruded material and eliminate unwanted flow instabilities at the device exit. In other embodiments, the flow focusing fluid is not provided, as described in further detail below.

In some embodiments, the density of the flow focusing fluid may be selected such that its density is substantially equal to that of the biopolymer solution extruded from the microchannels, such that the complex fluid remains neutrally buoyant during the formation process, contributing to the structural stability of the fluid network generated. For example, this may be achieved by the addition of glycerol.

Upon exiting microfluidic device 100, the spatial organization of the secondary biopolymer streams within the base layer is retained via a solidifying process to form a substantially planar solid material 130 with controlled heterogeneity. The fluid streams are emitted by the microchannels in the form of a three-dimensional array of complex fluid, which flow into an enclosed liquid filled horizontal reservoir. A narrow extrusion section is designed with the same cross-sectional area as that of the multilayered device exit region, for reducing flow instabilities during the extrusion process and thereby acting as a flow focusing geometry. The horizontal reservoir may be integrated with the microfluidic device (the substrate material of which would need to be thick enough to store the required volumes), or may be provided as an external reservoir that is interfaced with the microfluidic device.

Although the preceding example embodiments, and many of the embodiments and examples below, refer to the formation of planar biopolymeric materials from the controlled microfluidic dispensing of biopolymer solutions, it is to be understood that the scope of the present disclosure is not intended to be limited to materials formed from biopolymers. In other embodiments, solidifying process may be a polymerization process, gelation process, emulsification process, or other hardening process such that the planar sheet that emerges from microfluidic device is transformed into a planar material that is solid, physically resilient or in a substantially non-flowing state. It is to be understood that the term "solid", as used herein, includes soft materials such as hydrogels. The thickness of the planar heterogeneous material emerging from the device may be controlled, for example, by varying the flow rate of the base fluid and the extrusion speed.

Other suitable solidification methods include other forms of polymerization, including physical and chemical cross-linking. In some embodiments, the polymerization may be achieved by photopolymerization. In other embodiments, the polymerization may be achieved via free radical polymerization. For example, solidification may be achieved using a polymer such as polyethylene glycol diacrylate (PEGDA) with a commercially available photoinitiator Irgacure® 2595, or methacrylic alginate that is able to polymerize with both an ionic and a photo crosslinking reaction. Additionally or alternatively, thermally induced polymerization may be employed as a solidification method. For example, a solidified material may be obtained by thermally induced gelation of Matrigel and collagen, and mixtures of these with synthetic or natural hydrogels. Example hardening materials that may be employed include polymers such as PLGA, PLA, and mixtures thereof, and hydrogels including inter-penetrating polymer networks (IPNs) and other types of gelation (for example, shear-induced gelation of micelles).

It is to be understood that the polymer solution need not contain biopolymeric monomers, precursors, or other biomolecular species that form biopolymers. In some embodiments, polymerization may be performed such that the planar polymeric material is formed from a polymeric material other than a biopolymer.

One example process for solidifying the base and secondary polymer solution is a cross-linking process. For example, in some embodiments, the flow-focusing liquid, and/or the liquid into which the heterogeneous sheet emerges (e.g. the liquid within the horizontal reservoir), may contain a cross-linking species (such as an ionic species), and the base and secondary polymer solutions may include monomers or polymers that are cross-linked in the presence of the cross-linking species, such that cross-linking of the base and secondary fluid layer is initiated at or near the output of microfluidic device 100 where the base and secondary fluidic layer contacts the flow focusing liquid. Accordingly, the solidification of polymer solution or fluid streams forms a planar material with a spatial heterogeneity that is determined by the controlled dispensing of the secondary polymer.

As shown in the examples below, planar homogeneous and heterogeneous materials according to various embodiments have been produced with thickness ranging from approximately 100 µm to approximately 700 µm. It is to be understood that this thickness range is merely provided within the context of an example embodiment, and the in other embodiments, the thickness may be less than 100 µm, or in excess of 700 µm, depending on the choice of materials and the configuration of the microfluidic device. For example, in some embodiments, thin sheets having a thickness down to approximately 50 µm, or below approximately 50 µm, may be realized. FIGS. 2g, 2h, 5a and 5b provide an example 10-layer microfluidic 400 device that may be employed for performing selected embodiments of the present disclosure. In one embodiment, the microfluidic device layers are individually molded and vertically attached using a partial curing process[13], resulting in a 10-layer device able to withstand pressures up to 600 kPa. It is to be understood that this device is provided merely as an example, and that a wide variety of alternative device configurations are possible without departing from the scope of the present disclosure.

Referring first to FIGS. 5a and 5b, the microfluidic structure of the individual layers is shown. Layer 6 includes base microfluidic channels 420 forming the base microfluidic array and secondary microfluidic channels 430 forming the secondary microfluidic array, such that the base microfluidic channels 420 and the secondary microfluidic channels 430 distribute the base and secondary biopolymer solutions, and have their output apertures interleaved in a planar array near the output aperture 410 of the device. As shown in the Figure, the device includes a planar output channel 440 prior to the device output aperture. The length of planar output channel is configured such that the biopolymer solution emerges from an outlet of the planar output channel as a substantially planar liquid sheet.

Planar output channels 464 and 440 serve to distribute the flow focusing solution and the biomaterial sheet solution, respectively. In other words, planar output channels 464 and 440 merge the microfluidic channels into a fluid sheet (of either biomaterial (440), or flow focusing solution (464), or both; it is noted that in some embodiments, flow focusing layers are not included). For both flow focusing and biomaterial layers, multiple microfluidic channels are provided that encounter planar output channel prior to flowing out into the liquid reservoir, thus forming a single continuous sheet, as opposed to forming fibers.

In some embodiments, substantial polymerization of the liquid sheet is not initiated prior to the liquid sheet exiting the planar output channel (into the reservoir). For example, the device may be configured such that the reaction occurs due to contact between the polymer liquid sheet and one or both of the flow focusing solution and the additional solution residing in the reservoir, such that polymerization reaction is diffusion-based at and beyond the device exit.

In other embodiments, the polymerization reaction may be initiated within the planar output channel, prior to the liquid sheet exiting into the reservoir. For example, a pair of liquid sheets of flow focusing liquid may be formed above and below the liquid sheet of polymer solution within the planar output channel for initiating the polymerization of the liquid sheet. This may be achieved with a device in which the outlets of both the polymer distribution microfluidic array and the flow focusing arrays are in fluid communication with the inlet of the planar output channel, with the outlets of the polymer distribution array provided between the respective outlets of the two flow focusing arrays. Accordingly, the polymerization reaction could be made to occur within the planar output channel due to the contact between the flow focusing liquid sheets and the polymer liquid sheet.

In other example embodiments in which polymerization is initiated within the planar output channel, the polymerization reaction may be initiated by another mechanism, such as photopolymerization. In such an example embodiment, at least a portion of the device may be transparent to an incident photopolymerization light beam, in order to facilitate the photopolymerization reaction within the planar output channel. According to one embodiment, during operation of the device, secondary microfluidic channels 430 are interfaced (through vertical fluidic access ports, not shown in FIG. 5) with per-channel liquid dispensing or metering devices, such that the dispensing of the secondary biopolymer solution is controllable on a per-channel basis. In the present example embodiment, base microfluidic channels are interfaced with a single external base biopolymer solution dispensing device, which may be brought in fluidic communication with base microfluidic channels 420 through a network of base biopolymer solution distribution channels provided in layer 1. Accordingly, layer 1 is an optional initial distribution layer for evenly distributing the base layer from an initial microfluidic channel 450, through a series of branching points 452 to a plurality of microfluidic channels 454.

In other embodiments, base biopolymer solution microfluidic channels 420 may also be interfaced with per-channel liquid dispensing or metering devices, such that the dispensing of the base biopolymer solution is also controllable on a per-channel basis. In another embodiment, each microfluidic channel may be selectively connected to a source of base fluid and secondary fluid, such that either base fluid or secondary fluid may be selectively introduced into a given microfluidic channel.

In one embodiment, the device may include a single microfluidic array for dispensing one or more polymer solutions, as opposed to two separate arrays of microfluidic channels, as described in the preceding embodiments.

For example, in one embodiment, the device may include a single microfluidic array, where the inlet of each microfluidic channel in the array is connected, or connectable, to a common dispensing device for controllably dispensing a common polymer solution to all channels in the array. This embodiment provides a device that can be employed to produce a homogeneous planar polymeric material, such as a planar hydrogel sheet.

In another embodiment, a device for forming a substantially homogeneous planar polymeric material need not include an array of microfluidic inlets coupled to a planar output channel, and may instead include a single input channel that is in fluid communication with a planar output channel. In one example implementation, a device for forming a substantially homogeneous planar polymeric material may include a single input that is connected to a planar output channel by a structure similar in configuration to the flow focusing distribution layer that is shown in FIG. 5a, where a single inlet channel is connected to a planar output channel by a transition section 462 that is configured to produce a uniform planar fluidic output due to controlled fluidic resistance. In another embodiment, a single inlet channel may be connected directly to a planar output channel, where the planar output channel has a length sufficient for forming a substantially homogeneous liquid sheet prior to polymerization.

In another embodiment, each microfluidic channel in the array may be connected, or connectable, to a unique dispensing device, such that the dispensing of polymer solutions may be controlled on a per-channel basis for forming a planar polymeric material with controlled heterogeneity in composition.

In yet another embodiment, two or more of the microfluidic channels may be connected, or connectable, to a common dispensing device for dispensing a common polymer solution to a subset of the microfluidic channels in the array, and each remaining microfluidic channel in the array may be connected, or connectable, to a unique dispensing device for per-channel dispensing of one or more additional polymer solutions. One example of such an embodiment is an array of microfluidic channels where even or odd microfluidic channels are connected, or connectable, to a common dispensing device (e.g. for dispensing a base polymer solution), while each remaining microfluidic channel is connected, or connectable, to a unique dispensing device (e.g. for dispensing a secondary polymer solution).

In some embodiments, more than one type of polymer fluid may be selectively introduced into a given microfluidic channel, in order to provide increased diversity and control over the composition of the planar heterogeneous material.

Figure 5:
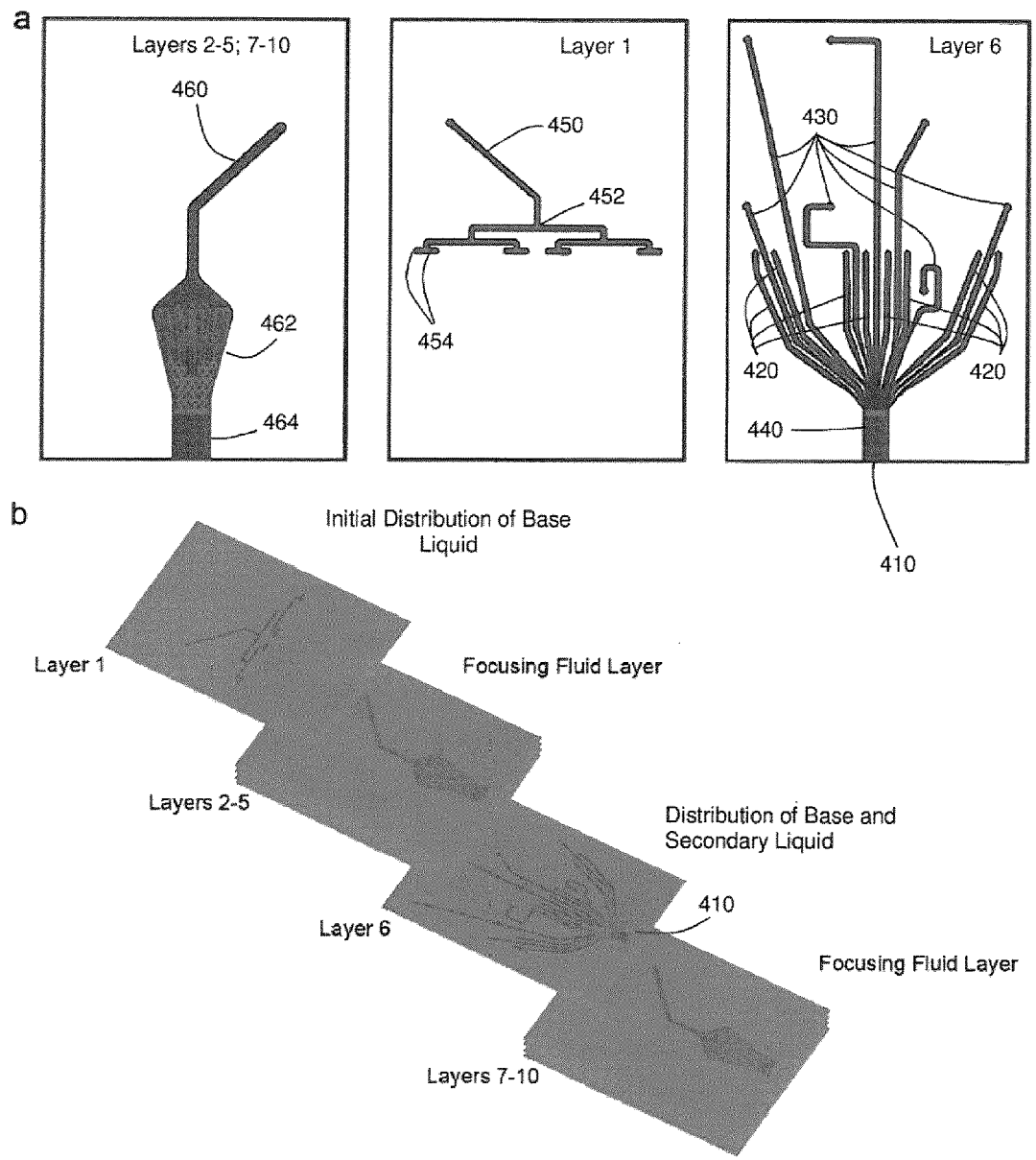
FIG. 5 shows (a) three microfluidic masters used in the fabrication of an example multilayer device, and (b) an illustration of the layers of a multilayered microfluidic device composed of 10 PDMS layers.

Referring again to FIG. 5, and as described above, in some embodiments, one or more flow focusing layers may be incorporated above and below layer 6. These layers are shown as layers 2-5 and 7-1 in FIG. 5b. Each flow focusing layer includes an input channel 460, which is directed through a fluidic resistive and distribution zone 462 in order to evenly spread the fluid over the width of flow focusing output channel 465. Upon sandwiching layer 6 between two flow focusing layers, the base and secondary fluid sheet emerging in planar output channel 440 is contacted, and focused, by flow focusing fluid in flow focusing output channels 465 (shown, for example, in FIG. 2b). FIG. 2g illustrates a microfluidic device 400 assembled based on the layers shown in FIG. 5, showing the various locations for providing the focusing fluid, base biopolymer solution, and secondary biopolymer solution.

The secondary polymer solution within the microfluidic channels may be dispensed and/or metered by any suitable liquid dispensing device. One or more components of the dispensing device may be incorporated on or within the microfluidic device. Suitable liquid dispensing devices and mechanisms include syringe pumps, peristaltic pumps, electronic or robotic pipettors, and valves with associate pressure devices. For example, in some embodiments, one or more reservoirs for the polymer solution may be included on the microfluidic device, and connected through valves to an external pressure regulation device for controlling the pressure in the head space above the reservoir.

An example of such an embodiment is shown in FIG. 2h, which provides an image of an example device 500 that includes integrated reservoirs 510 for providing and dispensing the secondary fluid on a per-channel basis. As shown in FIG. 2i, the pressure in the head space of each integrated reservoir is varied relative to atmospheric pressure by an external pressure regulation device and controllable valves. Accordingly, a single pressure regulation device (e.g. a pump) may be employed to establish a dispensing pressure level that is above atmospheric pressure, where the pressure applied to each reservoir headspace may be switched between the dispensing pressure level and atmospheric pressure by actuating valves (such as solenoid valves). In one example, the dispensing devices have a response time on a millisecond timescale, such as 10 milliseconds or less.

Referring now to FIG. 2a, an example embodiment is shown in which the solidified planar heterogeneous material 310 emerging from an example microfluidic device 300 is collected and drawn by a rotating drum 310, which rotates with tangential surface velocity $U_p$. The drum, or an alternative extrusion device, may be located at a suitable distance from the output of the microfluidic device so that the planar heterogeneous material (or homogeneous material, as described herein in alternative embodiments) is sufficiently strong or solid to be collected. The collected planar heterogeneous material may be further subdivided into individual sections, for example, for conducting separate assays or conducting cultures under different conditions.

As shown in the Figure, flow focusing liquid 340 is delivered to the microfluidic device 300 by gear pump 345, and base biopolymer solution 330 is delivered to microfluidic device 300 via an external syringe pump (the mechanisms and reservoirs for the delivery of secondary fluid are omitted in this figure for simplicity). The apparatus may also include an optical monitoring device 350, such as an imaging camera or microscope, which may also be employed to provide feedback for use in controlling the dispensing of liquids or other aspects of the process, based on the optical measurements.

As noted above, the planar polymeric material emerging from the microfluidic device 300 may be received in a liquid filled reservoir prior to being further processed (e.g. wound onto a drum and/or segmented into pieces). In one example implementation, the emerging planar material is passed through three sections: a device section where the microfluidic device sits, an extrusion section 360, and a collecting section 370.

Regardless of the polymerization process employed in this embodiment, the initially extruded fluid sheet may be first flow-focused in a narrow extrusion section, as this flow-focusing geometry minimizes formation of vortices at the microfluidic device exit, resulting in smooth fluid-interface between the biopolymer solution and the liquid filled reservoir, and thereby producing soft material sheet of uniform thickness.

In one example embodiment in which an ion-based polymerization process is employed to solidify the sheet, the liquid in external reservoir 360 may contain $Ca^{2+}$ ions to further cross-linking the extruded soft material sheet. In other example embodiments involving photo or thermal polymerization, the reservoir may contain a water-glycerol solution, with the glycerol serving strictly to balance the overall fluid density such that the extruded soft material sheet remains buoyant within external reservoir 360.

In the present example embodiment, third section 370 of the reservoir includes rotating drum 320 onto which the planar heterogeneous material sheet is wound. Rotating drum 320 is immersed (fully or partially) in liquid reservoir 370 in order to minimize surface tension effects at the air-liquid interface which would have detrimental effects on the general material sheet structure. In some embodiments, the base and secondary fluids contain hydrogel-forming precursors, such as certain biopolymers, that are solidified through a cross-linking process involving the diffusive transport of ions from the flow focusing fluid. As shown below, the planar hydrogel's properties (e.g. elasticity, diffusivity of different molecular payloads) can be tailored by controlling its microscale composition. However, it is to be understood that any solidification process may be employed to solidify the liquid sheet emerging from the microfluidic device, and that the scope of the present disclosure is not intended to be limited to the formation of planar heterogeneous hydrogel materials.

In some embodiments, secondary biopolymer solution 115 and base biopolymer solution 110 differ by composition such that they exhibit different structural, chemical, biochemical, mechanical, optical, elastic, or other properties. For example, secondary biopolymer solution 115 and base biopolymer solution 110 may differ only by the addition of a chromophore or a fluorophore.

In other embodiments, any polymer solution forming the planar biopolymeric material may include a payload. As further described below, in some embodiments, molecular, solid, particulate, liquid, and/or gaseous constituents may be provided within a polymer solution for incorporation into the planar polymeric material. In some embodiments, the payload may be a suspension and/or a solution.

Such embodiments may provide artificial biological systems, culture media and/or supports, reagent storage and/or delivery vehicles (e.g. microarrays), MALDI targets, and separation media (e.g. planar separation devices for chromatography or electrophoretic separation), with optional internal identification and/or quality control or calibration elements, among other selected example applications. The payload may include reagents for performing ligand-receptor assays, such as beads coated with antibodies for performing immunoassays, nucleic acids, aptamers, or other suitable binding and/or recognition species. Such reagents may be coated onto beads, which are provided as a payload.

In other embodiments, the payload may include biological molecules, cells, and/or tissues, for example, but not limited to DNA, RNA, biological molecules, proteins, growth factors, cytokines, tissues, pieces of tissues and organs.

In other example embodiments, the payload may include biodegradable beads or bubbles, optionally covered with reagents, affinity molecules or functional groups (specific or non-specific), or other bioactive molecules. Such an embodiment may be employed to produce a scaffold for cells to aggregate, where the scaffold, or a portion thereof, is biodegradable in situ, such that the scaffold degrades while aggregated cells produce an extracellular matrix.

Other example payloads for incorporation into any of the polymer solutions employed in the device include medicaments and flavor compounds, which may be employed in an embodiment where the polymer forming the planar polymeric material is edible and/or non-toxic. For example, the medicaments or flavor compounds may be provided in an encapsulated form to facilitate time-release and/or timed activity. The flavor compound may be selected such that the resulting planar polymeric material is suitable as a confectionary, or as another related item such as a breath odor control item. Other examples of payloads include fragrances and antiperspirants.

In other embodiments, the control over the spatial and temporal dispensing of secondary biopolymer solution 115 may be utilized to produce planar heterogeneous materials with pre-selected spatial concentration gradients of diffusing or binding molecules, which may be employed for directionally dependent mechanical and transport properties to be realized.

In addition to polymers and/or biopolymers, large diffusing or binding molecules, such as synthetic polymers, soluble factors, drugs, proteins and polysaccharides, can be controllably incorporated during the formation stage of the material. A variety of different molecules such as soluble and insoluble factors and drugs can be incorporated in the soft material with exquisite spatial control. Examples include polysaccharides and proteins using dextran, albumin, polylysine, and streptavidin.

The payload may include cells, thereby enabling cells to be co-localized and/or co-cultured within the same material substrate. In some embodiments, the planar heterogeneous material may be a soft substrate such as a hydrogel for maintaining cell viability, and base biopolymer solution 110 and/or secondary biopolymer solution 115 may include media or reagents suitable for cell culture and/or cell assays. Depending on the choice of liquid/fluid constituents (e.g.

polymers and payloads), tessellations and other microenvironmental conditions, the planar heterogeneous material may either display time-constant or dynamically changing characteristics. The programmable microscale composition of the planar heterogeneous material allows local and/or bulk properties to be controlled and tailored. As such, a wide variety of structures and applications may be realized according to variations of the embodiments disclosed herein.

In other embodiments, single and/or multiple cell types may be incorporated as a payload within the polymer solution. In tissue engineering applications, it is beneficial to authentically represent the physiological environmental milieu of a particular tissue or organ. Resembling the structure and function of tissues and organs requires multiple cell types and ECM molecules to be co-localized in two or three dimensional patterns at length scales that exceed several millimeters. Currently available cell patterning methods allow one to either incorporate multiple cell types in microparticles and subsequently organize them in one or two directions, or achieve co-localization along one direction within a fiber, but do not yet provide dynamic control over the matrix composition and the incorporation of multiple cell types in two or more directions.

Figure 4:
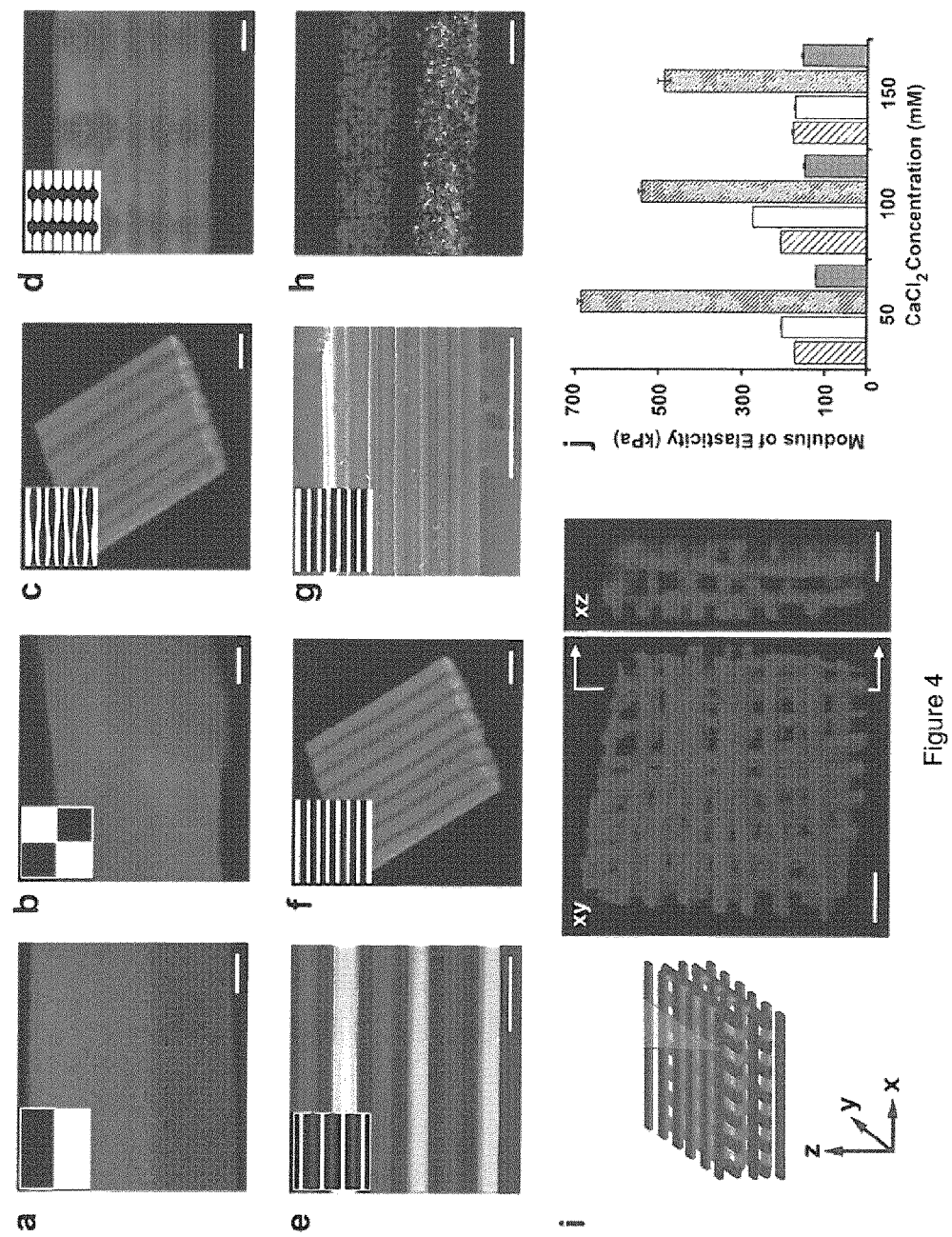
FIGS. 4a to 4h provide images of mosaic hydrogels with various tessellations, where two to three distinct material compositions are illustrated (insets represent schematic of desired patterns), including two parallel stripes (a), squares (b), alternating wave patterns (c), axially connected spots (d), and multiple parallel stripes (e-h) (continuous inlet gas pressures ranging from 2-14 kPa were used, with valve opening times between 50 ms and infinity (for continuous stripe patterns)), where g) provides SEM image of striped heterogeneous material and (h) provides wide-field fluorescence image of two parallel stripes containing 10 million cells/mL of cardiomyocytes (light gray) and fibroblasts (dark gray).
FIG. 4i shows millimeter-scale 3D organization of mosaic hydrogel sheets with tessellations corresponding to (f).
FIG. 4j plots the modulus of elasticity of homogeneous and mosaic hydrogels with $CaCl_2$ concentrations of 50, 100, and 150 mM: 2% w.t. alginate (dark gray), 1% w.t. pectin-1% w.t. alginate (lighter gray), 2% w.t. alginate with patterns of 1% w.t. pectin-1% w.t. alginate (light gray) as illustrated in (d), and (white) in (f).
FIG. 4k illustrates single (top) and multiple (middle and bottom) cell incorporation into a base planar material (top and bottom figures are fibroblasts (dark gray) and endothelial cells (light gray) at a cell density of 10 million cells/mL; middle figure consists of fibroblasts (dark gray) and cardiomyocytes (light gray) at a cell density of 2 million cells/mL; images were captured on Day 0); bottom figure consists of fibroblasts (dark gray) and endothelial cells (light gray).
FIG. 4l shows combinations of multiple cell types incorporated along with 6-bit barcoding of a planar material; scale bars 500 µm (a-h, k, l), 1 mm (i).

The ability to pattern multiple cell types in close geometrical proximity offers the potential of systematically exploring cell-cell interactions via secreted factors as well as the interrogation of heterotypic and homeotypic cell interactions. For example, FIG. 4*l* illustrates how the incorporation of different cell types can be combined with the ability to record the associated experimental parameters in the form of a barcode that can be tracked throughout the duration of cell culture.

Depending on its composition, the flow focusing liquid may or may not be incorporated into the solidified planar heterogeneous material. In some embodiments, a portion of the flow focusing liquid may be retained on or within the solidified planar heterogeneous material. For example, in the example embodiment described above, a cross-linking species is provided by the flow focusing liquid, and this cross-linking species forms a component of the solidified planar heterogeneous material. For example, in other embodiments, the flow focusing liquid is discarded after the output of the device.

In one example embodiment, the flow focusing liquid is itself solidified and forms layers of the solidified planar heterogeneous material. For example, the flow focusing fluid may include a constituent, such as a monomer, that can be hardened upon exit of the microfluidic device. The solidified flow focusing material may thus form an external solid coating around the internal planar heterogeneous sheet. According, in such an embodiment, the secondary polymer or biopolymer solution need not be solidified, and may be replaced by a composition that is incorporated as a solid, liquid, or gas. For example, in one embodiment, the secondary biopolymer or polymer solution may be replaced with a secondary liquid that maintains a liquid state after being locally dispensed, with the solidified base biopolymer or polymer solution and the solidified flow focusing layer locally encapsulating liquid droplets in the heterogeneous material. Such liquid droplets may form suitable volumes for performing chemical assays and/or culturing cells.

In another embodiment, as shown in the examples below, the secondary biopolymer or polymer may be replaced with a secondary liquid having a non-solidifying composition, such as a composition similar to or equal to that of the flow focusing liquid, such that the secondary liquid does not solidify upon exit from the microfluidic device. The resulting structure, having a Swiss-cheese-like topology with a network of holes formed therethrough, may be suitable for providing internal perfusion of cells with the planar material is formed into a three-dimensional multilayer structure.

In another example embodiment, the secondary biopolymer or polymer solution may solidify upon exit of the microfluidic device, but the composition of the secondary biopolymer or polymer solution (or a payload of the secondary biopolymer or polymer solution) may be selected such that its solid form, or a portion thereof, may be selectively removed without disturbing the structural integrity of the solid structural backbone formed from the solidified base material. For example, the solidified secondary material may be selectively removed by dissolving or etching in a suitable solvent.

Referring again to FIG. 1, an illustration is provided of how the selective control of the dispensing of secondary biopolymer solution 115 may be employed to produce planar heterogeneous materials with coded information 140 or tessellated structures 145. For example, spatiotemporal control may be achieved by incorporating a code (such as a binary code), wherein encoded bit has a volume on a nanoliter scale. Tessellated structures produced in this manner can exhibit directionally dependent properties, and therefore may allowed the local storage or the timed release of an embedded colloidal or biomolecular payload. Furthermore, tessellations of different hardenable materials may produce mosaic patterns with variable and controllable stiffness and/or diffusivity patterns. In some embodiments, features or bits may be encoded with a density of up to approximately 1 bit or spot per 200 µm in the flow direction (with the lateral direction density dictated by the relative spacing of the microfluidic channels).

A variety of patterns can be created within such continuously extruded planar heterogeneous materials. Selected example embodiments are demonstrated in examples below and through confocal and fluorescence microscopy by incorporating fluorescence microbeads into soft material. The size and shape of the secondary liquid component incorporated within the base liquid is dependent on the dispensing pressure Pi, base liquid flow rate $Q_M$, extrusion velocity Up, and dispensing actuation time. As shown below, confocal images of the planar sheet cross-section illustrate the shape of the material formed and can show that the patterned secondary liquid can spatially replace or displace the base liquid.

Although selected embodiments of the present disclosure describe methods of producing planar heterogeneous materials with coded information, tessellations, and/or spatial patterns, it is to be understood that in other embodiments, the planar heterogeneous material need not include geometrically repeating structures, information, or patterns. Some of the preceding embodiments, and the examples below, describe microfluidic devices in which one layer is provided for generating a planar heterogeneous material based on the dispensing and subsequently solidifying of a base biopolymer or polymer solution and a secondary biopolymer or polymer solution, wherein the dispensing of at least the secondary biopolymer or polymer solution is controllable on a per-microfluidic channel basis. However, it is to be understood that the present disclosure is not limited to devices having a single dispensing layer, and that in some embodiments, the microfluidic device may include two or more layers for producing planar heterogeneous sheets from base and secondary biopolymer or biopolymer solutions. A suitable number of flow focusing layers may be provided between each layer having base microfluidic channels and secondary microfluidic channels. For example, in one embodiment, a multi-layer device may be employed to produce multiple planar heterogeneous materials at the same time (i.e. in parallel).

Figure 14:
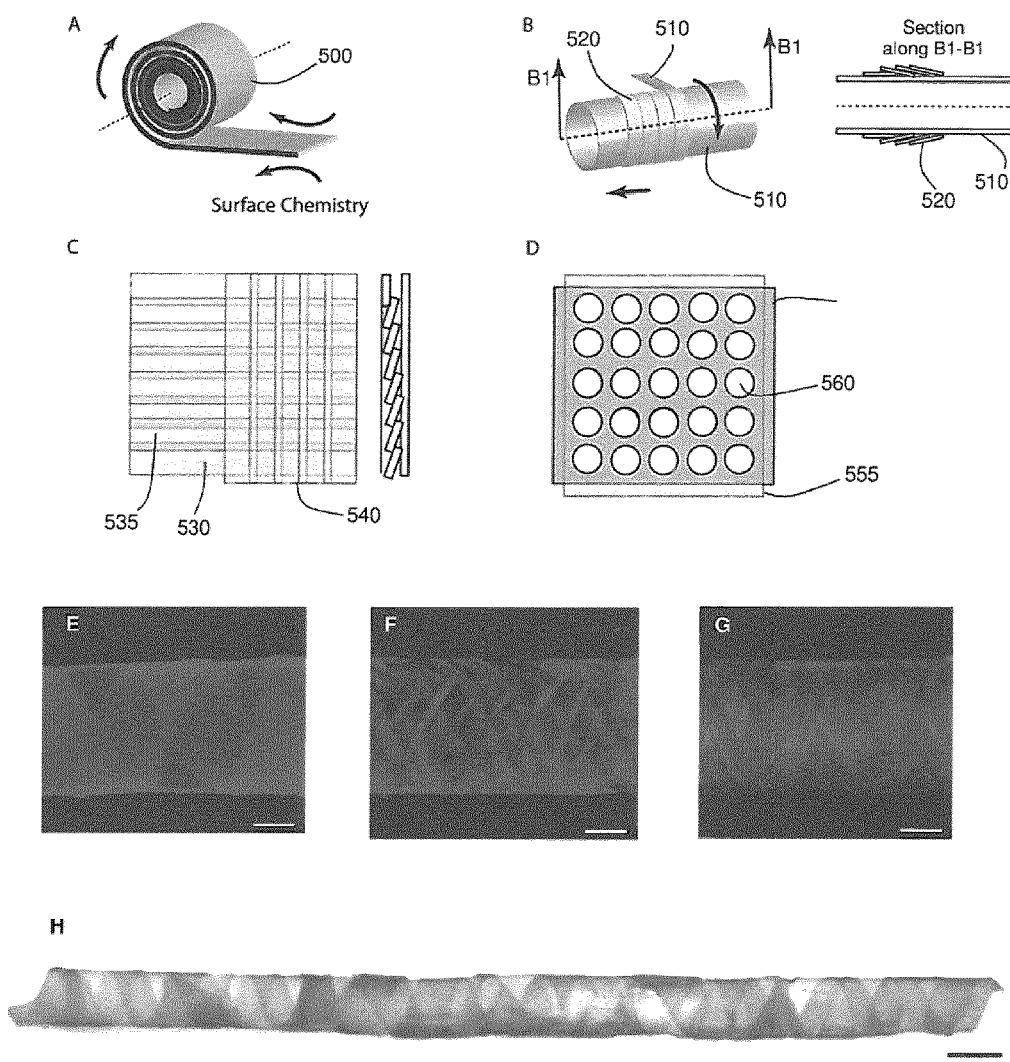
FIGS. 14 (a) to (h) illustrate several example embodiments of in-plane and vertical assembly of planar sheets, including (a) a rolled sheet forming a multilayered cylindrical structure, (b) an overlapping layered cylindrical structure formed by collecting a planar strip on a roller at an oblique angle, (c) an overlapping layered structure with overlapping layers in two lateral directions, (d) a vertically stacked structure formed from layers with patterned holes; and (e) to (h) show experimental realizations of the embodiment shown in FIGS. 14 (b) and (c).

Alternatively, the additional layer may be provided without including an additional flow focusing layer. For example, in one embodiment, a device may include a first array of microfluidic channels and an additional array of microfluidic channels in a stacked relationship, without an intervening flow focusing layer. FIG. 2j shows a planar biopolymeric material formed according to such an embodiment, in which a bilayer structure is formed from two adjacent arrays of microfluidic channels, each array dispensing a single biopolymer solution into a common planar outlet channel. The inset to FIG. 2j shows the bilayer planar biopolymeric material rolled into a multilayer configuration. According to selected embodiments, three-dimensional structures may be formed by layering planar heterogeneous materials formed according to the methods described herein. FIG. 14 illustrates several example embodiments of in-plane and vertical assembly of planar sheets to form layered structures.

In FIG. 14(a), a multilayered cylindrical structure 500 is formed by rolling a planar strip along a cylindrical axis. The strip may be rolled around a cylindrical object, such as rotating drum. The resulting three-dimensional structure may be employed to simulate a biological organ, such as a blood vessel, or another organ containing a lumen. The planar strip may be coated on one or both sides with a material suitable for adhering the adjacent layers of the formed structure, such as an adhesive or an appropriate surface functionalization or surface chemistry, which may be provided according to a chemistry implementation such as peptide chemistries, photochemistries and bioconjugation schemes. An adhesive or other desired coating may be applied to the planar strip during the extrusion process, for example, by incorporating the adhesive or other coating material within the flow focusing liquid, or within a liquid in the extrusion reservoir.

FIG. 14(b) illustrates another example embodiment, in which a planar strip 510 is layered as it is collected on a cylindrical support 510, thereby providing a composite layered structure 520 that has a cylindrical cross section, and extends longitudinally along an axis of the cylindrical support. This may be achieved, for example, by aligning the planar sheet at an oblique angle relative to the axis of the cylindrical support or roller.

A planar overlapping sheet embodiment is shown in FIG. 14(c), in which a plurality of planar strips are overlapped along two directions to form a structure that is extendable in two dimensions. As shown in the Figure, adjacent planar strips 530 and 535 are overlapped to create an extended structure along one dimension, and a second layer of overlapping strips 540 is provided to extend the structure along a second direction. Such an embodiment may be employed to create planar structures based on hydrogels, or other biocompatible materials, for applications in artificial skin and wound dressings.

FIGS. 14(e) to 14(h) show experimental realizations of the embodiments described above and shown in FIGS. 14(b) and 14(c). As an illustration, a rotating capillary tube (22-690-943, Fisher Scientific, Canada) was manually translated to collect a continuously extruded hydrogel sheet with 50% overlap in the sheet surface area. The overlap ensures the tubular architecture to be retained upon the removal of the capillary tube. Homogeneous and heterogeneous hydrogel tubes with inner diameters of approximately 1.5 mm and lengths of up to several centimeters were produced.

In FIG. 14(d), a porous vertically stacked structure is formed by vertically stacking planar layers 550 and 555, where planar layers 550 and 555 are created with holes 560 formed therein (for example, according to the embodiments described herein). In one embodiment, the successive layers may be aligned such that the holes in adjacent layers are spatially aligned. In other embodiments, the adjacent layers may be randomly aligned, or aligned with an offset in order to provide increased access to internal surfaces of the structure.

Such three-dimensional embodiments may be employed for applications involving automated 3D cell culture, combinations of cell culture and assays (e.g. bead assays), the scalable formation of 3D simulated tissues at physiologically relevant (organ) scales, 3D cell culture for multiple cell types, staining and imaging applications, bioreactors, photobioreactors, and artificial leaves via incorporation of microorganisms.

In some embodiments, as demonstrated in the examples below, different secondary biopolymer or polymer solutions may be provided to individual microfluidic channels of the device. Accordingly, such embodiments provide the ability to control both the heterogeneity in terms of time, space, and composition. In some embodiments, some of the secondary microfluidic channels may be provided for one or more payloads (e.g. cells or assay reagents), and other secondary microfluidic channels may provide chromophores, fluorophores, or other species for providing identification features (such as barcodes). Although the examples provided below disclose planar heterogeneous materials having widths on a millimeter to centimeter scale, it is to be understood that the width of the materials is not inherently limited, and may be increased by adding more microfluidic channels in the microfluidic array. Accordingly, the present embodiments may be adapted or scaled to provide wide planar materials, for example, with widths on a centimeter (or wider) scale, with arbitrary lengths due to the continuous nature of the extrusion process (the length scales with the extrusion time). For example, although the example embodiments have demonstrated widths up to approximately 3 cm, widths of on the scale of tens of centimeters (or more) may be attainable by modifying the device design.

In some embodiments, uniform thickness in the lateral direction may be achieved by configuring the channels such that the flow resistances of individual feed channels are substantially uniform. In other embodiments, the flow resistances could be chosen to be non-uniform and thereby produce sheets with a thickness gradient in a direction normal to flow.

As described further below, embodiments of the disclosure may be adapted for cell storage, transport, assays, identification and culture. In embodiments in which on-chip reservoirs are employed, a small dead volume (for example, less than approximately 15 µL may be selected to prevent cell settling. The demonstrated throughput of 160 µl/min may be suitable for applications in high-throughput screening. Furthermore, the extrusion process is compatible with sterile conditions, and may be implemented within an incubator. Additionally, in some embodiments, the planar heterogeneous materials described herein do not require a base substrate or physical template, and may be compatible with a variety of gelation chemistries (temperature, UV, ion exchange) and extracellular matrix constituents.

In one example embodiment, present embodiments may be adapted to provide a platform for continuous and automated soft material formation, cell incorporation, culture (and cell co-culture), staining and imaging. Such an embodiment could provide screening for more than 5,000 culture conditions (cell type(s), matrix material, soluble factors, dissolved gasses) in continuously defined and cultured biomaterial per day.

According to another embodiment, one or more diffusion barriers may be incorporated (for example, to obtain directed molecular transport of soluble factors, drugs, etc within the sheet) if the secondary and primary polymers have distinctly different diffusivities. Furthermore, the sheets may display stimulus responsive properties in response to environmental changes, such as pH changes. Accordingly, such properties may be employed to obtain a desired release-characteristic for drug delivery applications.

As shown in the examples provided herein, various secondary biopolymers may be incorporated within a planar, unsupported hydrogel sheet, at a sub-millimeter spatial resolution with a minimum feature size of approximately 100 μm or less. In other embodiments, the minimum feature size may be as small as approximately 50 μm. It is to be understood that the spatial resolution may depend on device and material parameters that include the feature sizes of the microfluidic channels, and the liquid viscosity. For example, smaller microfluidic channel feature sizes, and a correspondingly higher spatial resolution of the formed planar heterogeneous materials, may be achieved using a microfluidic device formed in silicon. The ability to precisely control the incorporation of the secondary hydrogel in the lateral direction, and in time, allows for the controlled generation various dispensing patterns or arrangements in the x, y-plane.

The following examples are presented to enable those skilled in the art to understand and to practice embodiments of the present disclosure. They should not be considered as a limitation on the scope of the present embodiments, but merely as being illustrative and representative thereof.

EXAMPLES

Example 1

Materials and Sample Preparation

Materials

Alginate (alginic acid sodium salt) and calcium chloride were purchased from Sigma-Aldrich (St. Louis, Mo., US). The alginate sample contained 2% w.t. alginate in a solution of 60% v/v glycerol in DI water. The pectin-alginate solution was obtained by incorporating 1% w.t. pectin (Sigma-Aldrich) into an aqueous solution containing 1% w.t. alginate and 65% v/v glycerol. The crosslinking solutions consisted of 50 mM, 100 mM, and 150 mM $CaCl_2$ in DI water containing 65%, 63%, and 61% v/v of glycerol respectively. The density of all solutions was 1.168 g/mL.

Two types of fluorescence microbeads were used either for continuously projecting wide-field fluorescence images of the formed hydrogels from an upright fluorescence microscopic setup (Nikon Eclipse E600, Nikon, Japan) onto a line camera (LC1-USB, Thorlabs, Newton, N.J., USA) or for off-line characterization using laser-scanning confocal microscopy (Olympus IX81 Inverted Microscope with FluoView FV1000, Olympus, Pennsylvania, USA). Specifically, microspheres with mean diameter of 1 μm with excitation/emission of 505/515 nm and 535/575 nm were purchased (F8852 and F8819, Invitrogen, Canada). Microbeads were added to the biopolymer solutions at a ratio of 1:600, followed by 20 min sonication (B5510-MT, Branson Ultrasonics, Danbury, Conn., USA) to minimize aggregation.

Neonatal Rat Heart Isolation

Neonatal Sprague-Dawley rats (1-2 day old) were euthanized according to the procedure approved by the University of Toronto Committee on Animal Care. The cells from the heart ventricles were isolated by treating with trypsin overnight (4° C., 6120 U/mL in Hanks's balanced salt solution, HBSS) followed by serial collagenase digestion (220 U/mL in HBSS)[43]. The supernatant from five collagenase digests of the tissues was centrifuged at 750 rpm (RCF=94×g) for 4 minutes, resuspended in culture medium, and pre-plated into T75 flasks (Falcon) for 1 h intervals to separate the adherent cells (non-myocyte) from the non-adherent cells (enriched cardiomyocyte).

Primary cardiac fibroblasts were obtained by cultivating for up to 7 days the cells adhered to the T75 flask during the pre-plating. Culture medium for both cardiomyocyte and fibroblast consisted of Dulbecco's modified Eagle's medium (DMEM) with 4.5 g/L glucose, 4 mM L-glutamine, 10% certified fetal bovine serum (FBS), 100 U/mL penicillin, 100 pg/mL streptomycin and 10 mM 4-2-hydroxyethyl-1-piperazineethanesulphonic acid buffer (HEPES) (Gibco, Invitrogen, Canada). Human umbilical vein endothelial cells (HUVEC) were purchased from Lonza, Canada.

Cell Patterning

Cells were suspended in a 1:1 ratio of cell suspension solution and RGDS (arg-gly-asp-ser) peptide-functionalized alginate solution. The cell suspension solution consisted of 12.3% v/v DI water, 1.2% v/v glucose solution (0.3 g/mL), 7.7% v/v 10× Medium 199 (Sigma-Aldrich, Canada), 1.1% v/v NaOH solution (1N), 2.0% v/v NaHCO3 solution (0.075 g/mL), 0.8% v/v HEPES (Invitrogen, Canada), 19.1% v/v Matrigel™, and 55.9% v/v collagen type I from rat tail (3.66 mg/mL, BD Biosciences, Canada).

The peptide functionalized alginate solution consisted of 1.5% w.t. RGDS-alginate and 0.08% w.t. collagen type I from rat tail. Peptide-functionalized alginate was obtained following a previously described procedure[44]. Briefly, RGDS peptide (American Peptide 44-0-14) was conjugated to alginate using carbodiimide chemistry with N-hydroxysulfosuccinimide ester (sulfo-NHS) stabilizer (Pierce, Fisher 24510). The resulted solution was purified by dialysis, dried by lyophilize, and stored at −20° C. until use.

Cell Tracking

CellTracker™ Red CMPTX (C34552, Molecular Probes, Invitrogen, Canada) was used for fibroblasts and CellTracker™ Green for cardiomyocytes (C2925, Molecular Probes). A 10 mM concentration of CellTracker™ dyes in DMSO was further diluted in serum-free culture medium (DMEM) to create a working concentration of 10 M. The cells were incubated in 1 mL of dye solution for 30 min at 37° C. in 5% CO2. Following the incubation step, the dye-cell suspension was centrifuged and the pellet was washed two times with DMEM.

Immunofluorescence Staining

Some cell samples were fixed in 4% paraformaldehyde in PBS at room temperature for 15 minutes followed by incubation in mouse anti-vimentin (Sigma, 1:100 dilution) overnight at 4° C. Samples were then incubated with anti-mouse Alexa 488 (Sigma, 1:100) at room temperature for 1 hour and imaged with confocal microscope (Olympus FV5-PSU confocal with IX70 microscope, Canada).

In other experiments, cell samples were fixed in 4% Paraformaldehyde in PBS at room temperature for 15 minutes followed by incubation in mouse anti-troponin T(Sigma, 1:100) overnight at 4° C. Samples were then incubated with anti-mouse TRITC (Sigma, 1:100) at room temperature for 1 hour, and imaged with confocal microscope (Olympus FV5-PSU confocal with IX70 microscope, Canada).

Tensile Testing

Tensile tests on planar samples of the cross-linked gel were performed in order to determine the stiffness for different microscale compositions. The modulus of elasticity of 1-2% alginate hydrogels were determined at different crosslinking concentrations (50, 100, 150 mM) using an Instron tensile tester.

Samples were cut to lengths of approximately 20 mm and fixed with a cyanoacrylate adhesive (Krazyglue Advanced Formula, Elmer's Products, Columbus, Ohio, USA) to cardboard strips, which were vertically clamped between tensile grips for testing. A ramp of 0.1 mm/s was applied using a 1000 g load cell until failure.

Bulk elastic moduli were calculated from the obtained stress-strain curves in the linear-elastic region, for both samples produced by free extrusion and wheel-extrusion. All samples measurements were obtained and averaged from n=5. Free extrusion produced mechanically weaker planar soft material compared to wheel-extrusion, potentially due to the alignment of the alginate molecules under tension in the latter case, resulting in mechanically more robust planar materials. In addition, increasing the concentration of $CaCl_2$ in the crosslinking bath from 50 mM, 100 mM, and 150 mM generally increased the gel stiffness.

Sample Preparation for Scanning Electron Microscopy

Hydrogel samples were fixed in 2% glutaraldehyde in a 0.05M sodium cacodylate buffer at pH 7.4 for 1 hr at room temperature, followed by gradual replacement of the liquid phase with 100% ethanol. Dehydration of the samples was achieved with liquid $CO_2$ at 10° C. in a critical point dryer. Samples were subsequently heated to 31° C. with a pressure increase to 7.2 MPa, transitioning the $CO_2$ to supercritical fluid conditions. Lowering the pressure from the supercritical state allowed a direct transition into the gas phase without causing any unwanted liquid-gas phase transitions. The dehydrated sample was then transferred into a vacuum and vapour-deposited with a thin film of gold to render the outer surface of the substrate electrically conductive.

Example 2

Microfluidic Device Fabrication

The microfluidic device consisted of 10 vertically stacked and bonded PDMS layers that were individually obtained by moulding from different masters. FIG. 5 represents a rendered view of the microfluidic device design and its various components.

Masters with 150μm tall features were defined by spin coating negative photoresist SU8-2050 (MicroChem Corp, Newton, Mass., USA) onto clean glass substrate. The final feature height was achieved by two spin coating steps at 1600 rpm (30 s with a 5 s linear ramp to 1600 rpm), producing a 75μm thick resist layer in each step. This two-step procedure ensured thickness uniformity across the entire master. After the first spin coating step, the substrate was postbaked for 6 min at a temperature of 65° C., followed by 15 min at 95° C. Following the second spin coating step, the substrate was baked for 10 min at 65° C. and 35 min at 95° C.

Features with minimum width of 230 μm at the device exit section were patterned by soft lithography with 24 mW/cm² UV intensity and 9 s exposure time (total energy of 220 mJ). The exposed substrate was baked for 30 s at 65° C. and 20 min at 95° C., left to cool to room temperature, and developed under constant shaking for 12 min with SU8 developer (MicroChem Corp). FIG. 5 illustrates a rendered exploded view of the various layers that are part of the final microfluidic device.

Individual layers of the microfluidic device were defined by spin coating[44] poly(dimethylsiloxane) (1:10 ratio of curing agent to monomer) (PDMS, Sylgard 184 Silicone Elastomer Kit, Dow Corning, Midland, Mich., USA). Spin coating PDMS at 450 rpm for 30 s resulted in layers with uniform thickness of 400±7 μm. The multilayer device was obtained by sequentially aligning and bonding individual layers that were previously partially cured for 8 min at 80° C., producing a final multilayer device composed of 10 layers.

Microfluidic channels within different layers were connected by manually puncturing through holes using a 19 gauge blunt needle. Other means of forming holes, including laser ablation or molding holes, may alternatively be employed.

On-chip reservoirs were obtained from 3 ml BD syringe barrels cut in half, resulting in a total fluid storage volume of 1.5 ml. The section of the barrel containing the female Luer lock connector was used for easy connection to the computer-controlled solenoid valves using male Luer lock connectors (Upchurch Scientific, Oak Harbor, Wash., USA). These reservoirs were implemented onto the microfluidic device by first fixing with epoxy and subsequently pouring a 1 cm thick uncured PDMS layer over the final device, preventing the reservoirs from delaminating. The completed multilayer microfluidic device was further cured for 8 hrs at 80° C. Devices consistently withstood inlet pressures up to 600 kPa without any delamination.

Example 3

Formation of Planar Heterogeneous Hydrogels

Figure 2:
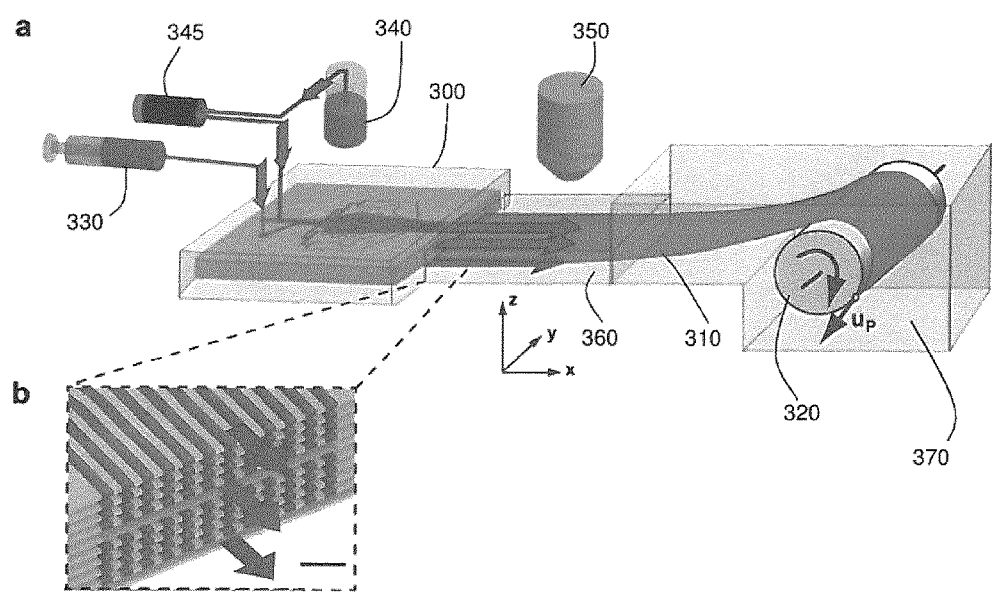
FIG. 2 illustrates a system for the continuous formation of hydrogel sheets, showing (a) an example apparatus consisting of a microfluidic device with inlets for a base biopolymer solution and focusing fluid; (b) an illustration of the fluidic exit portion of the microfluidic device, (c) a photograph of fluidic exit portion of the microfluidic device; (d) a graph demonstrating control over planar soft material thickness by varying drum rotation speed UP, with base biopolymer flow rate QB=▲60 µl/min, ●90 µl/min, ■120 µl/min; (e) and (f) SEM images showing the pore structure of planar biopolymer of homogeneous composition: (e) 2% w.t. alginate, (f) 1% w.t. pectin-1% w.t. alginate; (g) an illustration of the microfluidic device for the formation of planar heterogeneous materials; (h) a photograph of multilayered microfluidic device with on-chip reservoirs for the supply of biopolymers 1-7 into a base biopolymer; (i) a schematic of valve actuation and pressurization of on-chip reservoirs (scale bars 1 mm (b, c), 2 µm (e, f), 5 mm (g, h)); (j) bilayer structured formed from device with stacked microfluidic arrays (inset shows rolled bilayer).
Figure 2J:
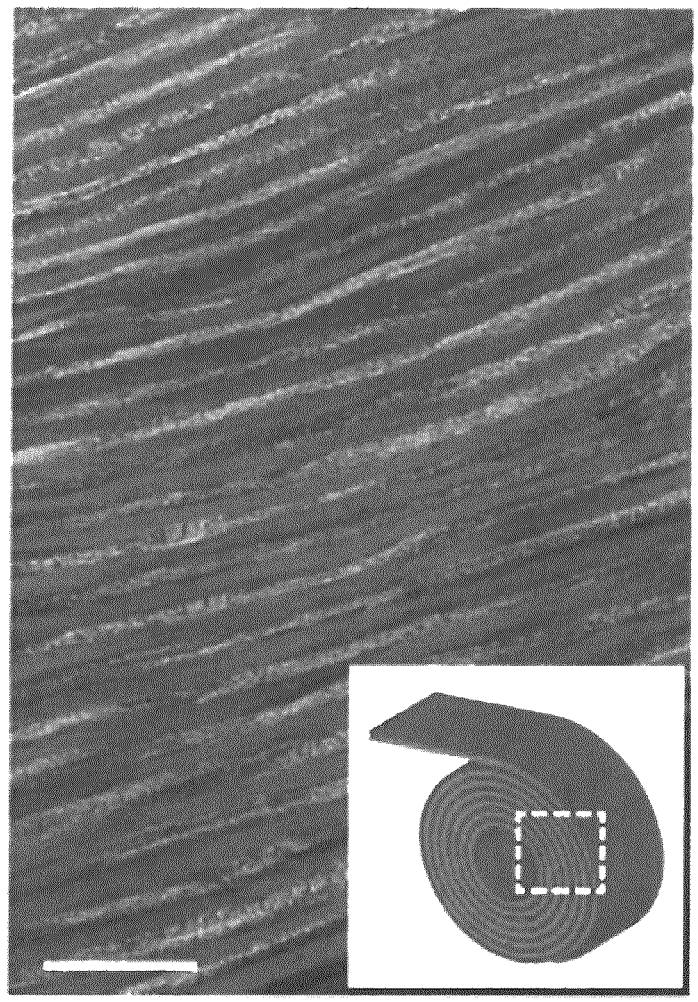

Planar heterogeneous hydrogels (thickness δ=150-350 μm, width ~3 mm) were formed using a multilayer microfluidic device along with the experimental setup shown in FIG. 2. As noted above, device layers were individually molded and vertically attached using a partial curing process,[13] resulting in a 10-layer-device that was able to withstand pressures of up to 600 kPa (FIG. 5). The center layer (indicated as layer #6 in FIG. 5) carried to the device exit via a set of parallel microchannels a time-varying content of biopolymer solutions. Additional layers located above and below delivered the crosslinker at the device exit (FIGS. 2a-c).

The produced biopolymer sheet flowed into a liquid-filled reservoir containing flow focusing liquid (see FIG. 2a, and description provided above). To reduce the unwanted effect of flow instabilities at the device exit and to ensure a uniform and controlled sheet thickness, δ, two co-flowing fluids were delivered from above and below the soft biopolymer sheet in a flow-focusing configuration. The focusing fluids carried cross-linking ions and induced gelation of the sheet. In the present example, a 2% w.t. alginate solution was used, which is a biopolymer with well-known biocompatibility[16] and ionic crosslinking mechanism.[17] To increase the fluid viscosity and render the produced biopolymer sheet neutrally buoyant with respect to the focusing fluids, glycerol was added to both the biopolymer and focusing streams, with the latter containing $CaCl_2$ as the crosslinker.

The focusing fluids were continuously supplied by an annular gear pump (mzr-2921, HNP Mikrosysteme, Parchim, Germany) at a rate of 8 mL/min. At a location approximately 50 mm downstream of the device exit, the sheet was manually attached to a collection drum (21.3 mm in diameter) that rotated at a constant tangential velocity, $U_P$ (FIG. 2a).

Figure 6:
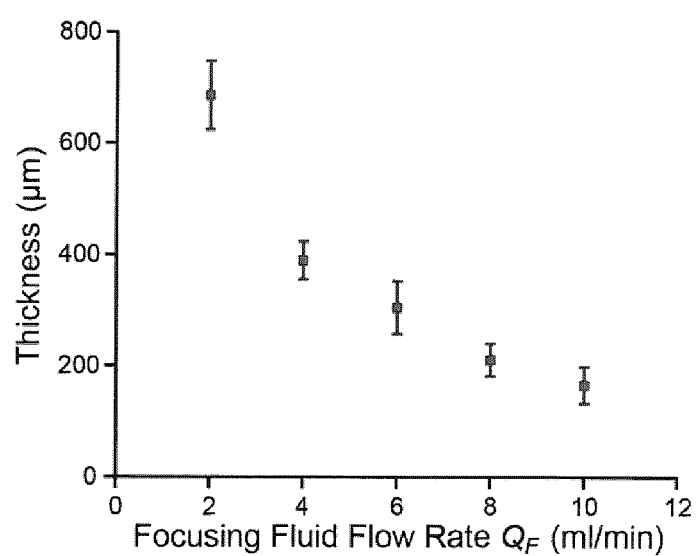
FIG. 6 plots the dependence of material thickness on the flow rate of the focusing stream QF, and for QB=120 µl/min, demonstrating control over soft material thickness.
Figure 7A:
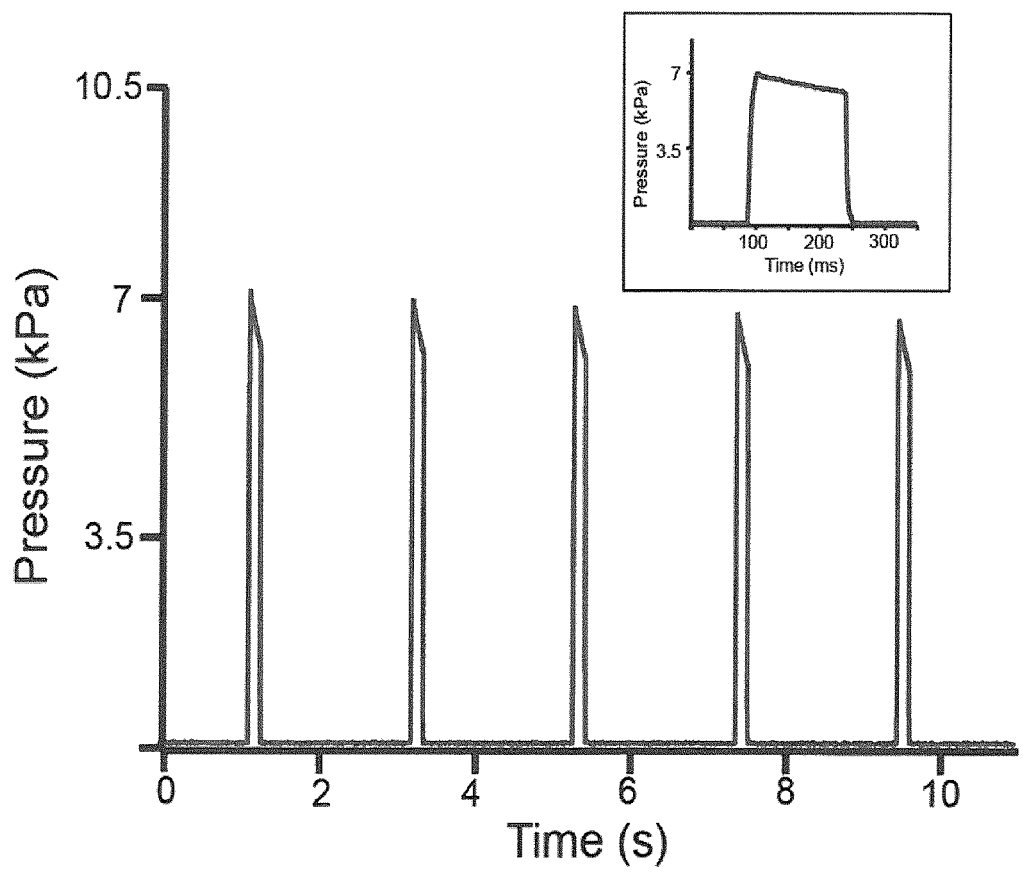
FIG. 7 plots the time dependence of pressure in on-chip reservoirs, for a valve activation pattern of: (a) 0.15 ms open-2 s close, and (b) 0.25 ms open-2 s close (input pressure 7 kPa; insets represent magnified view of pressure evolution during valve actuation).
Figure 7B:
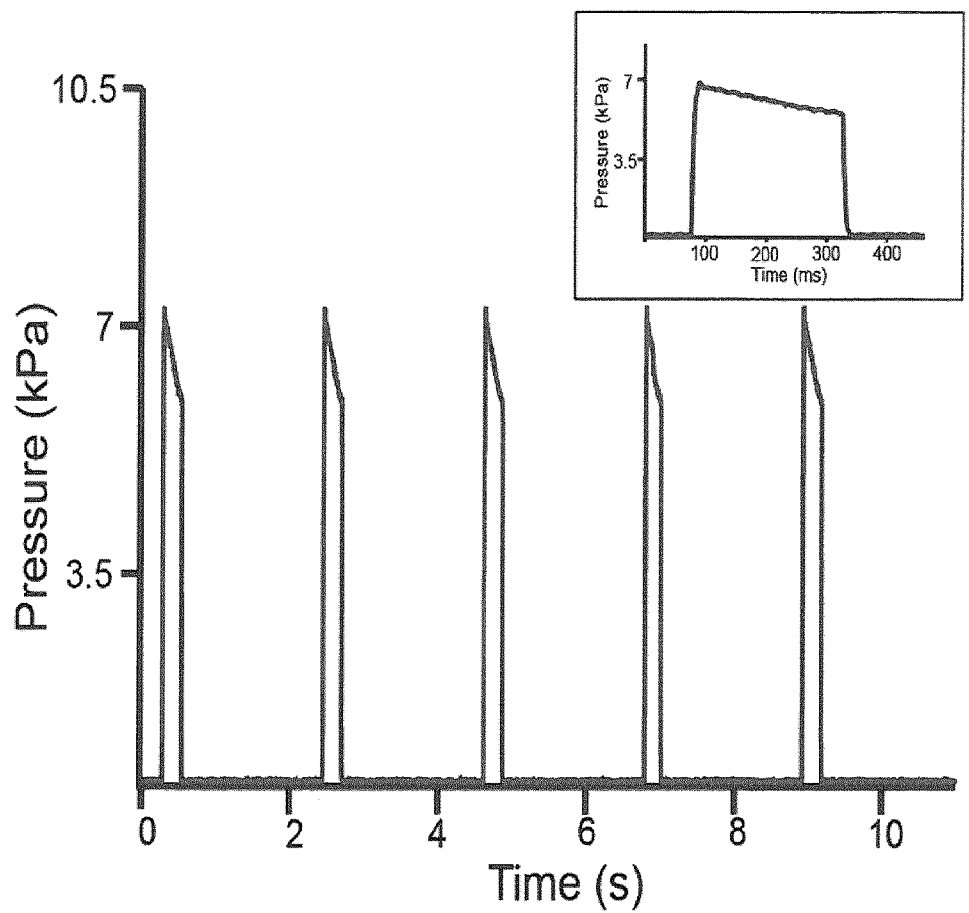

Planar hydrogel sheets with well-defined thicknesses were also produced without additional pulling via the collection drum, by relying exclusively on the shear imposed by the focusing fluid. Thickness of samples produced at $Q_B$=120μl/min and $Q_F$=2-10 ml/min was characterized. Thicknesses ranging from 170-700 μm were obtained and measured by optical microscopy of the cross section (FIG. 6).

Computer-controlled solenoid valves (The Lee Company, Connecticut, US) (FIG. 2g-i and FIG. 7) initiated the outflow of secondary biopolymers from one of the seven on-chip reservoirs during a time period tV at which the head pressure was raised from the atmospheric pressure level P1 to P2. A biopolymer spot was then predictably incorporated within the hydrogel sheet and cross-talk between different reservoirs was prevented. Accordingly, continuous gas pressure, ranging from 0.3-2 psi, was supplied to 7 solenoid valves which open/close to pressurize/depressurize their respective on-chip reservoir, with valve actuation response time of 10 ms.

Characterization of the dynamic behaviour of the computer-actuated solenoid valves (model LHLA0521111H, The Lee Company, Westbrook, Conn., USA) was achieved using piezoresistive pressure transducers (pressure range: 0-30 psi, time resolution: 1 ms, model HSCDIP030PGAA5, Honeywell, Morristown, N.J., USA). On-chip measurements obtained in the reservoirs during valve actuation in terms of a voltage were converted to a pressure reading using a calibration curve. Two actuation cycles were considered: 0.15 s open and 2 s closed, and 0.25 s open and 2 s closed. The measured pressures and valve actuation times were found to be in good agreement with the programmed input parameters.

After having drawn an initial amount of the sheet around the drum, the flow focusing pump was stopped, and the hydrogel sheet continuously exited the device and was collected by the drum (some focusing fluid remained in contact with the fluid sheet departing from the output of the microfluidic device, such that delivery of $CaCl_2$ ions was maintained for initiating the solidification of the planar material via crosslinking). Although the shear stress exerted by the focusing fluid alone was sufficient to consistently form hydrogel sheets (as demonstrated in FIG. 6), the rotating drum was employed for this purpose, as this configuration allowed the continuous formation, image-based inspection, and collection of mosaic hydrogels.

The sheet thickness δ was dynamically controlled by varying the flow rate of the base biopolymer, QB, using a syringe pump (model PHD, Harvard Apparatus, Massachusetts, US) and by varying UP (FIG. 2d).

Figure 12:
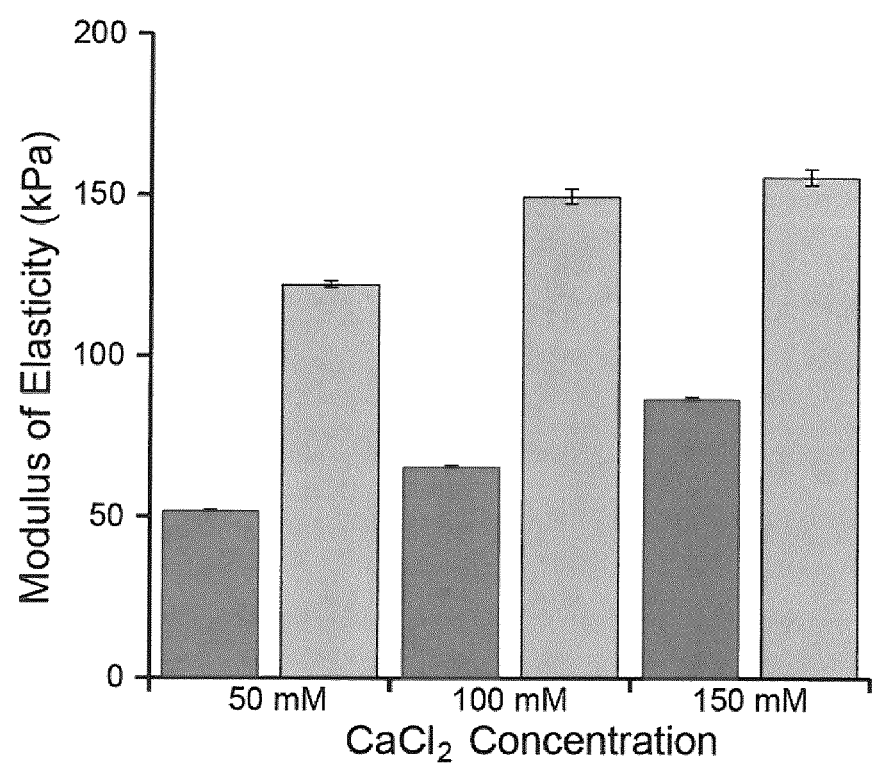
FIG. 12 plots the modulus of elasticity for a homogeneous soft material, composed of 2% w.t. alginate that was produced in the free-extrusion (dark grey) and pulled-extrusion modes (light gray).

To elucidate the effects of material formation procedure on elasticity, the moduli of elasticity of soft material samples produced in the free-extrusion and pulled-extrusion modes were measured. The employed base biopolymers and their pore sizes (FIGS. 2e,f) along with the increased alignment of the polymer fibers due to the axial stress imposed by the pulling drum affected the elastic moduli of the produced sheets (see FIG. 12). In general, samples obtained in the pulled-extrusion mode exhibited increased moduli of elasticity as compared to those formed in the free-extrusion mode. Without intending to be limited by theory, it was hypothesized that this difference was caused by a promoted alignment of the alginate molecules during the pulling process.

Example 4

Spatiotemporal Control and Payload Incorporation

The experimental apparatus 300 shown in FIG. 3a was used to assess the spatiotemporal control of the process. A computer interface provided control over each reservoir through the solenoid valves described above, allowing individual localized spots of the secondary biopolymer to be dispensed on demand.

In one experiment, the secondary biopolymer was substituted with a viscosity-matched aqueous solution having a composition identical to the focusing fluids (i.e., it contained 50 mM $CaCl_2$). A planar soft material sheet with an array of void areas was obtained, shown in FIG. 3b, by periodically dispensing the viscosity-matched aqueous solution from each secondary microchannel, at the following experimental conditions: Up=10 mm/s, QB=200 μl/min, inlet pressure P=3.5 kPa, and tv=65 ms.

In a second experiment, the extent to which the incorporated biopolymer replaced the base biopolymer was investigated by first employing fluorescently labelled microspheres as the payload. Confocal microscopic scans were performed and found the smallest ellipsoidal spot (lengths of semi-principal axes: 100 μm [w], 130 μm [L], 130 μm [δ]) that completely replaced the base hydrogel across the entire sheet, as shown in FIG. 3c. The spot was produced with the conditions Up=12 mm/s, QB=160μl/min, inlet pressure P=3.5 kPa, and tV=50 ms.

Figure 13:
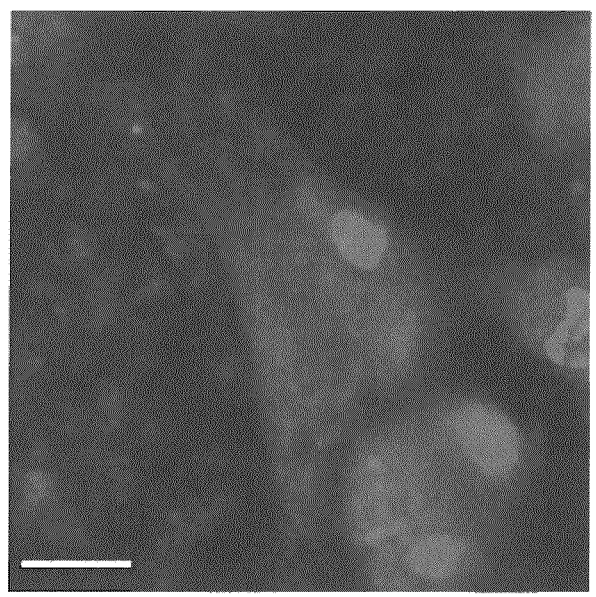
FIG. 13 is a confocal fluorescence image of cardiomyocyte attachment within a patterned hydrogel sheet (40×, Day 5); scale bar 10 µm.

In a third experiment, viable cells were selected as the payload. The secondary biopolymer was modified to improve cell viability and functionality, since alginate alone is insufficient to promote cell proliferation, attachment, and migration [21, 22]. A payload of neonatal rat cardiomyocytes at a density of 10 million cells/mL was suspended in a peptide functionalized hydrogel solution (as described above). Upon day 3, beating of cardiomyocyte clusters was observed. Preliminary cell attachment was also observed and is illustrated in FIG. 13.

Figure 8:
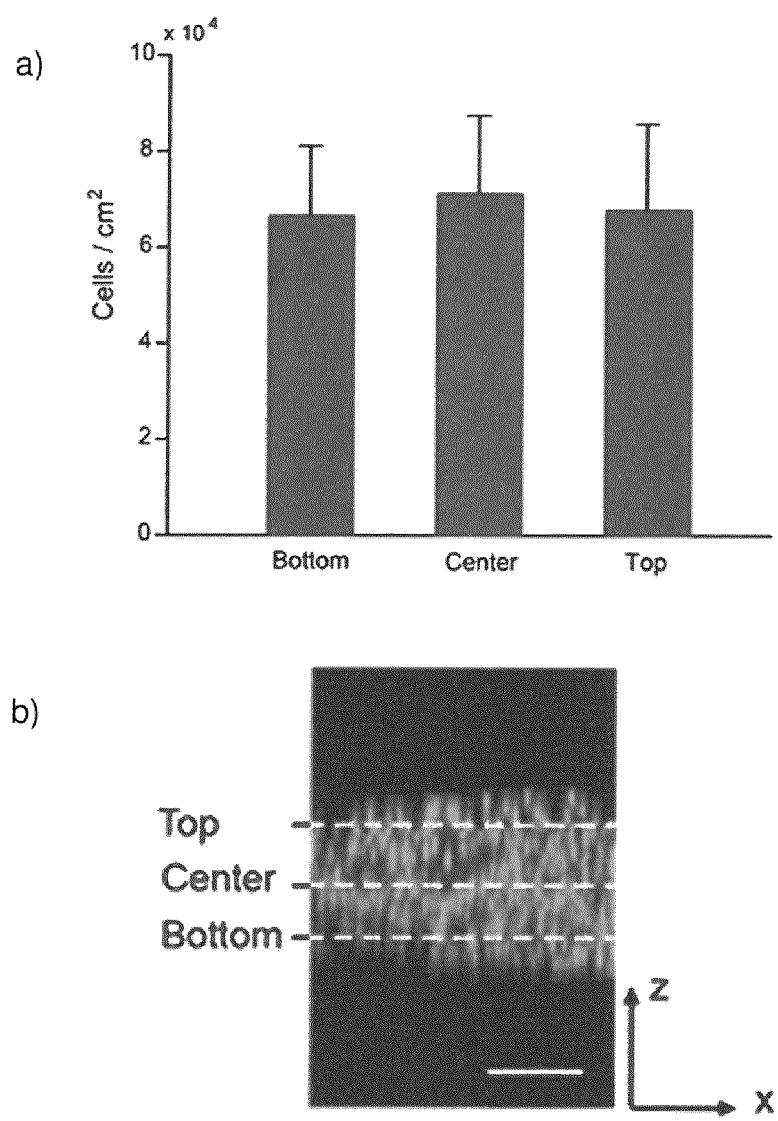
FIG. 8 shows (a) a graph showing statistics of cell distribution within a single pattern (n=5), according to the image shown in (b); scale bar 200 µm.

The homogeneous distribution of cells within the hydrogel sheet was assessed by z-stack confocal scans of five spots containing cardiomyocytes pre-labelled with Cell-Tracker™ Green (Molecular Probes, Invitrogen, Canada) and incorporated at a density of 10 million cells/mL. Z-stack scans were collected with a 30 μm step size to prevent cells from being counted twice. For each spot sample, three slices located in the middle, top, and bottom, were selected and cells were counted from these x-y plane slices within an area of 400×400 $\mu m^2$ (as shown in FIGS. 8a and 8b).

Confocal microscopic scans revealed a uniform distribution of cardiomyocytes across the hydrogel sheet, shown in FIG. 3(d), in a configuration that is not attainable in a single step using conventional top-down patterning approaches. The cell-loaded secondary biopolymer pattern clearly extended throughout the entire cross-section (see FIG. 8) of a sheet sufficiently thin (δ~250 μm) to be adequately penetrated by oxygen and nutrient molecules contained in the culture solution.

The fact that δ is at least tenfold greater than the average size of the incorporated cells renders mosaic hydrogels a candidate format for 3D cell culture. Although the presently described approach has been demonstrated to produce sheet thicknesses of up to at least δ~700 μm (see FIG. 6), thicknesses of δ>250 μm were not considered for 3D cell culture as internal vascularization would be required to ensure cells remain viable throughout the cross section.

In another cell-based experiment, fibroblasts were suspended in the same secondary biopolymer as the cardiomyocytes and were incorporated as patterned spots at a cell density of 10 million cells/mL. Confocal fluorescence images of the patterned spots obtained on Day 5 revealed the cells ability to attach onto the hydrogel matrix, as shown in FIGS. 3e and f. Patterned sheets were fixed and immunostained following the protocol described above.

In a fourth experiment, the secondary biopolymer consisted of alginate containing fluorescently labeled diffusible molecules (concentration 100 μM, molecular weights 4 kDa and 40 kDa FITCdextran, and 10 kDa rhodamine-dextran, Sigma-Aldrich, Missouri, US). Spots of the secondary biopolymer (~4 nL in volume) were incorporated in either 2% w.t. alginate (I) or in 1% w.t. pectin-1% w.t. alginate (II) and the diffusive release of the fluorescent marker was followed in time-sequences of fluorescence micrographs. FIG. 3g shows two fluorescence images that were taken from such a sequence for a spot with a 40 kDa FITC-dextran payload, the first one right after gelation and the second one 3 hrs later.

The diffusion coefficient for molecular transport of dextran (4 kDa, 10 kDa, and 40 kDa) through two different hydrogel matrices that were composed of either 2% w.t. alginate or 1% w.t. pectin-1% w.t. alginate were calculated by curve fitting the time-lapsed experimental data with the analytical solution for one dimensional diffusive transport into a semi-infinite domain[9]:

$$I(x, t) = I_0 \mathrm{erfc}\left(\frac{x}{2\sqrt{Dt}}\right).$$

The resulting diffusivity, plotted in FIG. 3h, was obtained for a best fit using the least mean squares method (LMS). The LMS value is defined as the sum of the residuals squared, $S=\Sigma_{i=1}^{n} r_i^2$, where the difference between the experimental intensity value and the value predicted by the model is $r_i = I_{exp,i} - I(x_i, t)$.

For all considered molecular payloads, a higher diffusivity was consistently obtained for hydrogel (I) as compared to hydrogel (II), an effect that was attributed to the larger average pore size of hydrogel (I) that was confirmed by scanning electron microscope (SEM) images shown in FIGS. 2e and f. As expected, the diffusivity in both base hydrogels decreased as the molecular weight of the payload increased.

Example 5

Encoding of Information

The ability to incorporate isolated spots of a secondary biopolymer into unsupported solidified sheets allows information to be encoded in a compact manner. In the present experiment, illustrated in FIG. 3a, the secondary biopolymer alginate contained fluorescent microspheres as the payload. At a location downstream of the device exit, the encoded information was continuously projected onto a line camera using a fluorescence imaging configuration.

The precise spatial and temporal control over the pattern formation (~80 μm, 10 ms) enables the use of these material patterns as means of encoding high density information within the extruded planar material. A Labview interface was designed to program the actuation of 7 valves to write, in the form of patterns, analog as well as digital information.

As a demonstration of this capability, the word 'TORONTO' was patterned onto the extruded template material in approximately 14 s, with QM=160 μl/min, Pi=0.5 psi, Up=12 mm/s. Valves were actuated at a pressure of P2=3.5 kPa with opening and closing times of 75 ms and 1000 ms, respectively. The velocity of the drum was UP=12 mm/s. Each letter was represented by 7-20 individual spots and occupied an area of approximately 6.25 mm².

Fluorescence image and line camera intensity measurements of the encoded word were obtained by labeling matrix solution with Nile red microbeads, with the results shown in FIG. 3h. Ultimately, the short valve response time of 10 ms and the small achievable spot size of approximately 80 μm offer higher information density, which can be achieved by encoding words and texts in a digital fashion, using 7 digit binary numbers that can be converted into standard ASCII codes and converted back into text. This was achieved by assigning the 7 valves to 7 digits in the standard ASCII binary code. The information to be patterned can be programmed into the valve actuation Labview interface and the resulting encoded planar material is continuously read by a line camera as it is being extruded. A Matlab code was designed to read the intensity information recorded from the line camera, convert it into binary numbers, and subsequently translate back into a text. As an illustration, the word 'TORONTO' was encoded within approximately 7.5 s.

Similarly, cardiomyocytes as a payload were pre-labelled (CellTracker™ Green, Molecular Probes, Invitrogen, Canada) and incorporated in multiple spots that represented the letters "T" and "O" (FIG. 3i). The base biopolymer was 2% w.t. alginate and the secondary biopolymer was a suspension of 10 million cells/mL in the same peptide-functionalized hydrogel as described previously for cardiomyocytes.

The density of the encoded information was increased 19 fold by employing the 7-bit American Standard Code for Information Interchange (ASCII) where each of the seven solenoid valves was assigned to one bit. The intensity values recorded from the formed hydrogel sheet were interpreted by a custom computer program, translated back into text and validated against the original text. In ASCII format, "TORONTO" was incorporated within a 37.5 mm long hydrogel sheet during approximately 7.5 s at QB=160 pl/min and UP=8.25 mm/s (FIG. 3j).

To demonstrate the ability of consistently writing and reading information, article 1, chapter 1 of the UN Charter (165 words and 1,047 characters including spaces) was encoded in the same format (see FIG. 3k and FIG. 9). A 5.6 m long sheet was produced within 18.8 min and subsequently validated the encoded information with 100% accuracy.

Example 6

Geometric Control Over Mosaic Hydrogel Properties

The ability to dynamically control the local material composition provides an effective means of altering local and bulk material properties, such as the permeability and the elasticity, and of creating soft materials with directionally dependent properties. In the present example, mosaic hydrogels were formed and characterized, using confocal and wide-field fluorescence microscopy, with a variety of tessellations including square tiles (FIG. 4b), stripes of variable width (FIG. 4c), axially interconnected spots (FIG. 4d) and sections of uniformly wide stripes (FIGS. 4a, e-h).

In another experiment, the obtained mosaic hydrogel sheets were vertically stacked to produce 3D assemblies with a defined non-isotropic composition. To illustrate this approach, five hydrogel sheets with patterns corresponding to the ones shown in FIG. 4f were stacked such that individual patterns were rotated by 90 degrees in between neighboring layers. In order to increase contrast between the two biopolymer solutions during a confocal fluorescence scan, only one of the biopolymers contained a payload of fluorescence microspheres. The resulting 3D structure had dimensions 5 mm [x]×5 mm [y]×1.5 mm [z] (FIG. 4i).

In cases where the base hydrogel and the secondary biopolymer were chemically distinct from each other (i.e., they did not differ by the presence or absence of a payload only), the effect of the different tessellations on the bulk elastic modulus was studied. Homogeneous and mosaic alginate sheets were formed via cross-linking with three $CaCl_2$ concentrations, 50, 100, 150 mM, and tensile tests were conducted (Custom 840LE2 tensile tester, Test Resources Inc., Minnesota, USA) (FIG. 4j, see above for procedure). Two homogeneous hydrogel samples with compositions (I) and (II) (see Example 4) were prepared, along with mosaic hydrogels with the tessellations shown in FIGS. 4d and 4f.

FIG. 4j summarizes the elastic moduli that were obtained for the different crosslinker concentrations. The values obtained for mosaic hydrogels fall in between the ones corresponding to homogeneous samples. A comparison between the two mosaic hydrogels suggests that axially aligned tessellations (FIG. 4f) resulted in higher elastic moduli than laterally aligned ones (FIG. 4d).

All samples exhibited an increase in the bulk elastic modulus when the crosslinker concentration increased from 50 mM to 100 mM. As the concentration of $CaCl_2$ increased, the crosslinking rate increased proportionally. As a result, a mosaic hydrogel with a locally increased stiffness in proximity of the sheet surface was formed, limiting the diffusion of $CaCl_2$ into the hydrogel and thereby creating weaker internal polymer networks. Without intending to be limited by theory, it was believed that the decrease in elastic modulus that was observed at 150 mM was associated with this effect.

Example 7

Planar Co-Localization of Single and Multiple Cell Types

In the present example, experiments were conducted to demonstrate continuous two-directional patterning of cardiomyocytes, endothelial cells and fibroblasts, major components of the native heart[29,30], at a resolution of ~400µm and at length scales of several millimeters. The cellular payloads suspended in the biopolymer streams are exposed to shear levels less than 2 dyne/cm² while passing through the microfluidic device (FIG. 10), which is within physiological ranges[31-33] and well below shear stresses of 167-200,000 dyne/cm² commonly associated with directprinting[26] and ink-jet printing strategies.[34-36]

Figure 11:
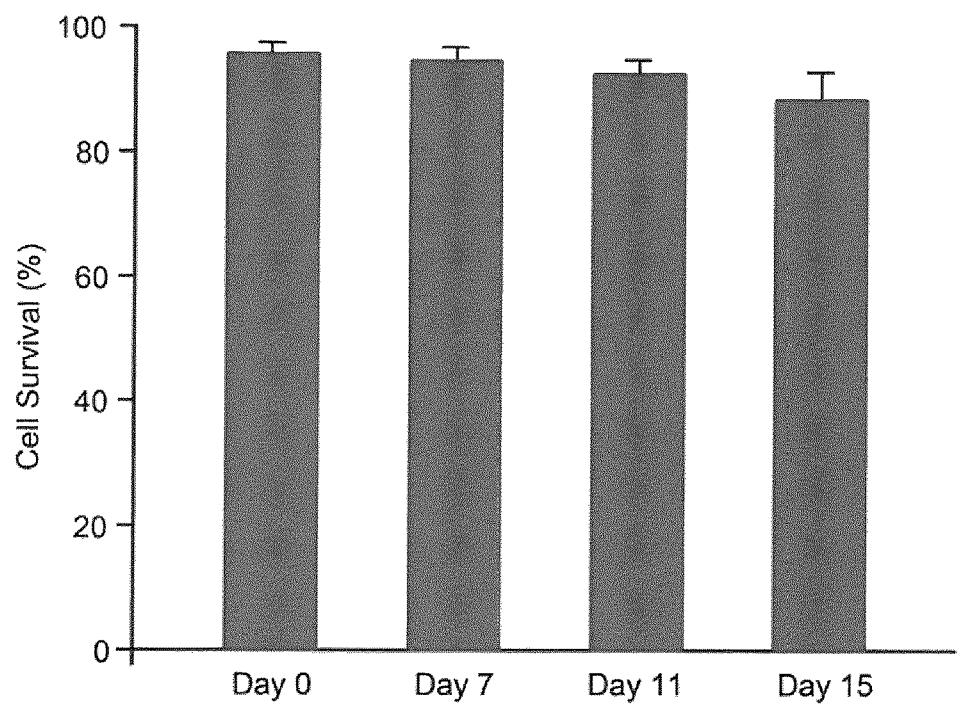
FIG. 11 plots results from studies of survival of fibroblasts when incorporated into a patterned hydrogel sheet (n=5).

Neonatal rat fibroblasts were incorporated at a concentration of 10 million cells/mL and the conditions $U_p$=12 mm/s, QB=160 µl/min, inlet pressure P=3.5 kPa, and $t_r$=65 ms (FIG. 4k, top panel). Cell survival within 15 days of culture was investigated using a Live/Dead viability/cytotoxicity kit for mammalian cells (L3224, Invitrogen, Canada), resulting in 88.7% viability on Day 15 (FIG. 11). The co-localization of two cell types (cardiomyocytes or endothelial cells with fibroblasts) within separate tessellations within a mosaic hydrogel was illustrated by patterning parallel stripes (FIG. 4h) or islands (FIG. 4k, center and bottom figures).

FIG. 4l illustrates how the incorporation of different cell types can be combined with the ability to record the associated experimental parameters in the form of a barcode that can be tracked throughout the duration of cell culture. Patterns consisting of cardiomyocytes (light gray) and fibroblasts (dark gray) were co-localized using four on-chip reservoirs. The remaining three reservoirs were dedicated to a 6 bit computer-readable code where a 2% w.t. alginate with 5% v/v fluorescence microspheres (P8819, Invitrogen, Canada) was used as the secondary biopolymer.

Example 8

Shear Stress During Cell Patterning

Shear stresses during the flow of cell suspension into the microfluidic device were calculated to ensure that the shear stress experienced by the cells did not exceed physiological levels. Given the employed microfluidic channel geometry and experimental conditions, the inlet pressures (wells) of 2-4 kPa and a viscosity of the (uncrosslinked) biopolymers of approximately 0.05 Pa·s, the shear stress is linearly distributed between the location of the channel center (zero) and its maximum value of 13-26 dyne/cm² at the wall (Poiseuille flow).

Figure 10:
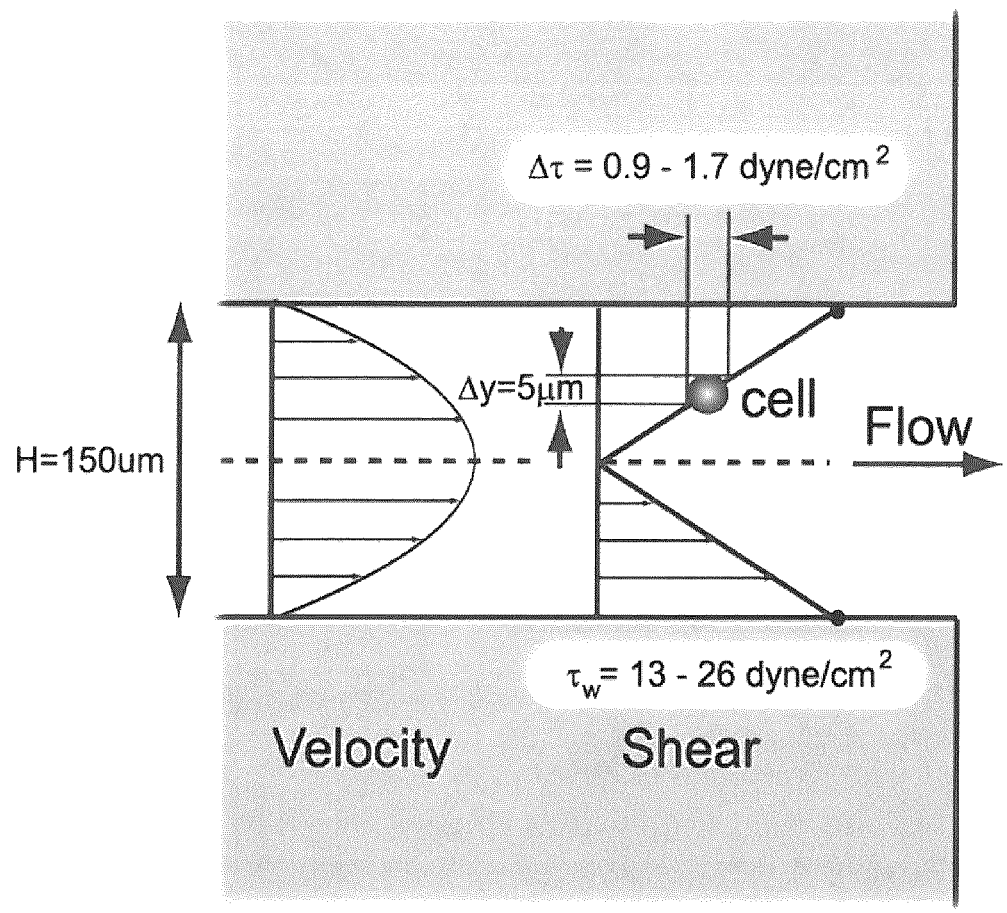
FIG. 10 is an illustration of the shear stress profile within a microfluidic channel.

The cells suspended within the biopolymer are therefore subjected to shear stresses less than 2 dyne/cm² (as shown in FIG. 10), a level well within physiological conditions. Endothelial cells, e.g., experience 15-20 dyne/cm² in undisturbed regions of the vascular system, can be transiently exposed to 40-50 dyne/cm² in areas of disturbed flow[45,46] and exhibit reduced adhesion above 100 dyne/cm²[47].

The calcium chloride concentrations of 50-100 mM that were used for cross-linking of hydrogel sheets are consistent with conditions previously employed for cell encapsulation and are not detrimental to cells[5-7].

Example 9

Formation of Wide Hydrogel Sheets without the Use of Flow-Focusing Streams

Figure 15:
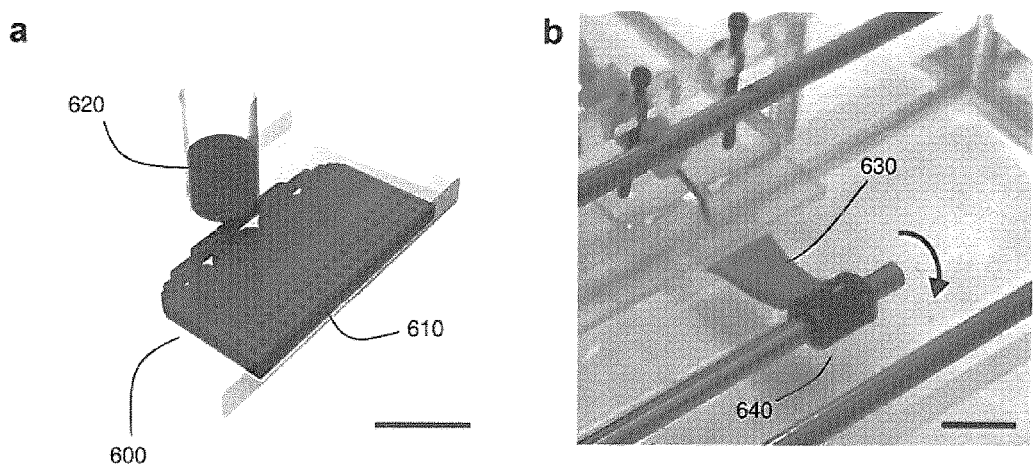
FIGS. 15(a) and (b) show an example implementation of a device for forming a wide homogeneous hydrogel sheet without the use of flow-focusing streams, showing (a) a rendered schematic of microfluidic device containing a single layer for the extrusion of a planar homogeneous soft material sheet that is 3 cm in width, and (b) a close-up photograph obtained during a running experiment where a homogeneous 3 cm wide soft material sheet is produced and collected onto the rotating drum, without the use of flow-focusing streams (the device illustrated in (a) was used). Scale bars are 1 cm (a), and 3 cm (b).

The present example illustrates the following ability to form planar hydrogel sheets having a width significantly exceed that described in the preceding examples. FIG. 15(a) is a rendered schematic of the microfluidic device containing a single layer for the extrusion of a planar homogeneous soft material sheet, where the width of the device aperture 610 is 3 cm. An on-chip reservoir 620 can be used to supply the desired biopolymer solution while minimizing dead volume. FIG. 15(b) is a photograph obtained during a running experiment, where a homogeneous, 3 cm wide, planar soft material sheet 630 is produced and collected onto rotating drum 640. Unlike some of the aforementioned embodiments, the present example device was fabricated and operated without the use of flow-focusing streams. Furthermore, the present example device was implemented using a single biopolymer solution for forming a substantially homogeneous biopolymeric sheet.

Example 10

Figure 16A:
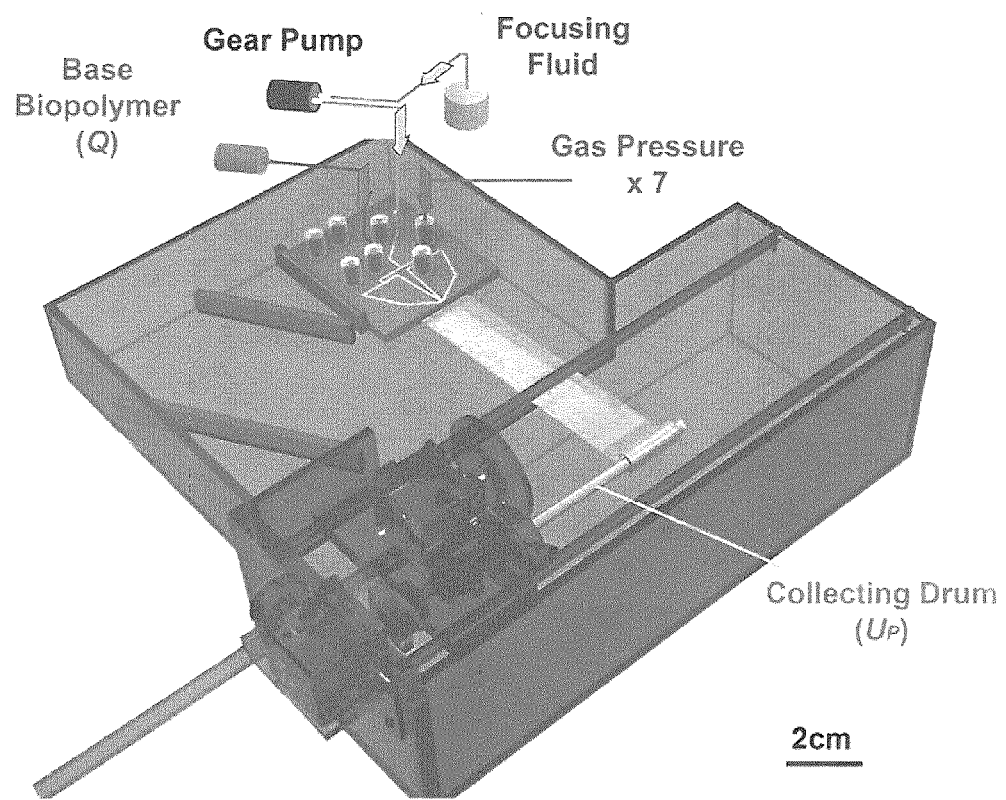
FIGS. 16(a) and (b) show an example implementation of a device for forming a planar biopolymeric material, including (a) a rendering of the example device placed within the liquid filled reservoir and (b) a photograph of an experimental implementation of the device placed within the liquid filled reservoir.
Figure 16B:
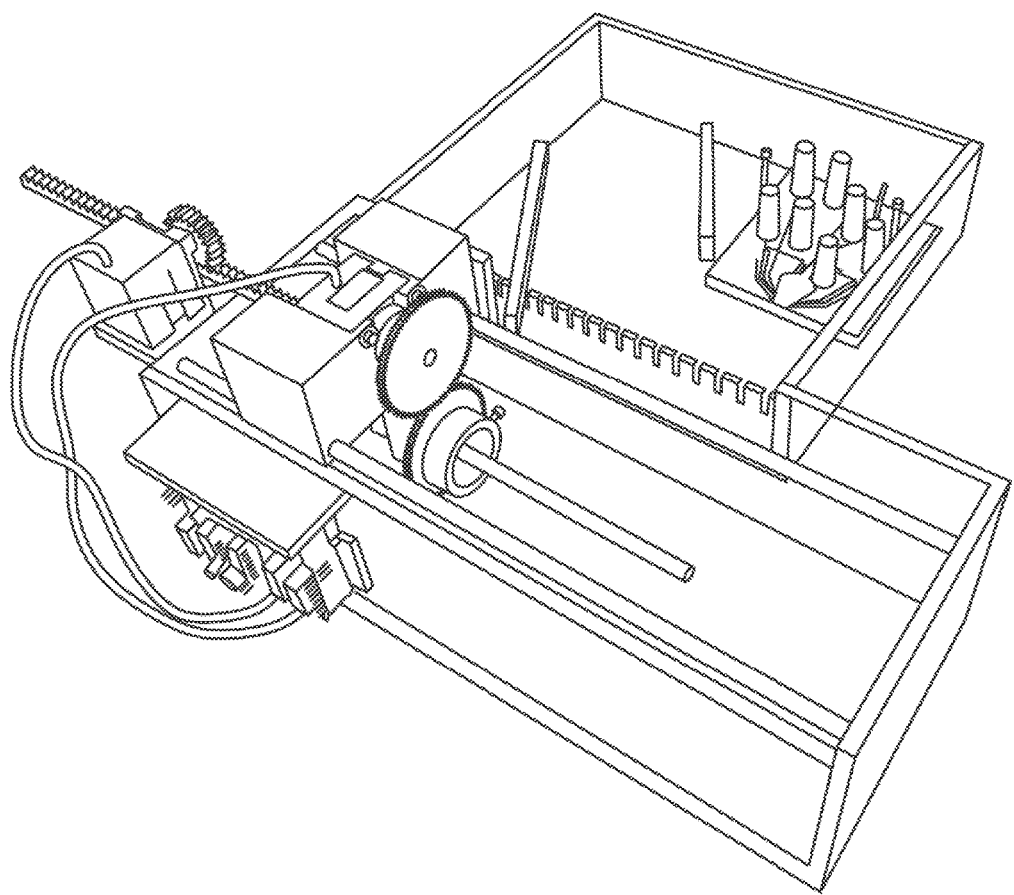

Experimental Implementation of Apparatus for Forming Planar Biopolymeric Material The experimental implementation of the apparatus is described as follows. FIG. 16(a) is a rendered illustration of an example device placed within a liquid filled reservoir for the formation of a planar biopolymer sheet. The rendered example device is supplied with a base biopolymer solution which flow rate Q is controlled by a syringe pump, up to seven same or distinct secondary biopolymer solutions which are distributed using gas pressure through seven on-chip reservoirs, and a flow focusing solution that is supplied using a gear pump. Upon exit of the planar biopolymer solution into the liquid filled reservoir, a diffusion-based reaction triggers the solidification of the biopolymer fluid into a biopolymer sheet which is subsequently collected onto a drum that rotates at velocity Up. FIG. 16(b) is a photograph of the rendered experimental embodiment illustrated in FIG. 16(a).

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. Bong, K. W., Bong, K. T., Pregibon, D. C. & Doyle, P. S. Hydrodynamic focusing lithography. *Angewandte Chemie—International Edition* 49, 87-90 (2010).
2. Dendukuri, D., Pregibon, D. C., Collins, J., Hatton, T. A. & Doyle, P. S. Continuous-flow lithography for high-throughput microparticle synthesis. *Nature Materials* 5, 365-369 (2006).
3. Glotzer, S. C. & Solomon, M. J. Anisotropy of building blocks and their assembly into complex structures. *Nature Materials* 6, 557-562 (2007).
4. Kim, J. W., Larsen, R. J. & Weitz, D. A. Synthesis of nonspherical colloidal particles with anisotropic properties. *Journal of the American Chemical Society* 128, 14374-14377 (2006).
5. Walther, A. & Muller, A. H. E. Janus particles. *Soft Matter* 4, 663-668 (2008).
6. Whitesides, G. M. & Grzybowski, B. Self-assembly at all scales. *Science* 295, 2418-2421 (2002).
7. Chung, S. E., Park, W., Shin, S., Lee, S. A. & Kwon, S. Guided and fluidic self-assembly of microstructures using railed microfluidic channels. *Nature Materials* 7, 581-587 (2008).
8. Bowden, N., Terfort, A., Carbeck, J. & Whitesides, G. M. Self-assembly of mesoscale objects into ordered two-dimensional arrays. *Science* 276, 233-235 (1997).
9. Kang, E. et al. Digitally tunable physicochemical coding of material composition and topography in continuous microfibres. *Nature Materials* 10, 877-883 (2011).
10. Choi, N. W. et al. Microfluidic scaffolds for tissue engineering. *Nature Materials* 6, 908-915 (2007).
11. Tan, W. & Desai, T. A. Microscale multilayer cocultures for biomimetic blood vessels. *J. Biomed. Mater. Res. Part A* 72A, 146-160 (2005).
12. Ladet, S., David, L. & Domard, A. Multi-membrane hydrogels. *Nature* 452, 76-U76 (2008).
13. Unger, M. A., Chou, H. P., Thorsen, T., Scherer, A. & Quake, S. R. Monolithic microfabricated valves and pumps by multilayer soft lithography. *Science* 288, 113-116 (2000).
14. Knight, J. B., Vishwanath, A., Brody, J. P. & Austin, R. H. Hydrodynamic focusing on a silicon chip: Mixing nanoliters in microseconds. *Physical Review Letters* 80, 3863-3866 (1998).
15. Anna, S. L., Bontoux, N. & Stone, H. A. Formation of dispersions using "flow focusing" in microchannels. *Applied Physics Letters* 82, 364-366 (2003).
16. Augst, A. D., Kong, H. J. & Mooney, D. J. Alginate hydrogels as biomaterials. *Macromolecular Bioscience* 6, 623-633 (2006).
17. Fang, Y. et al. Binding behavior of calcium to polyuronates: Comparison of pectin with alginate. *Carbohydrate Polymers* 72, 334-341 (2008).
18. Chen, C. H., Shah, R. K., Abate, A. R. & Weitz, D. A. Janus particles templated from double emulsion droplets generated using microfluidics. *Langmuir* 25, 4320-4323 (2009).
19. Nie, Z. H., Li, W., Seo, M., Xu, S. Q. & Kumacheva, E. Janus and ternary particles generated by microfluidic synthesis: Design, synthesis, and self-assembly. *Journal of the American Chemical Society* 128, 9408-9412 (2006).
20. Derda, R. et al. Multizone paper platform for 3D cell cultures. *Plos One* 6 (2011).
21. Nagakura, T. et al. Effect of viscous injectable pure alginate sol on cultured fibroblasts. *Plastic and Reconstructive Surgery* 116, 831-838 (2005).
22. Pokrywczynska, M., Drewa, T., Jundzill, A. & Lysik, J. Alginate is not a good material for growth of rapidly proliferating cells. *Transplantation Proceedings* 40, 1664-1667 (2008).
23. Radisic, M. et al. Oxygen gradients correlate with cell density and cell viability in engineered cardiac tissue. *Biotechnol Bioeng* 93, 332-343 (2006).
24. Kuo, C. K. & Ma, P. X. Ionically crosslinked alginate hydrogels as scaffolds for tissue engineering: Part 1. Structure, gelation rate and mechanical properties. *Biomaterials* 22, 511-521 (2001).
25. Du, Y., Lo, E., Ali, S. & Khademhosseini, A. Directed assembly of cell-laden microgels for fabrication of 3D tissue constructs. *Proc Natl Acad Sci USA* 105, 9522-9527 (2008).
26. Bruzewicz, D. A., McGuigan, A. P. & Whitesides, G. M. Fabrication of a modular tissue construct in a microfluidic chip. *Lab Chip* 8, 663-671 (2008).
27. Qi, H. et al. Patterned differentiation of individual embryoid bodies in spatially organized 3D hybrid microgels. *Adv. Mater.* 22, 5276-5281 (2010).
28. Fernandez, J. G. & Khademhosseini, A. Micro-masonry: construction of 3D structures by microscale self-assembly. *Adv. Mater.* 22, 2538-2541 (2010).
29. Naito, H. et al. Optimizing engineered heart tissue for therapeutic applications as surrogate heart muscle. *Circulation* 114, I72-78 (2006).
30. Brown, M. A., Iyer, R. K. & Radisic, M. Pulsatile perfusion bioreactor for cardiac tissue engineering. *Biotechnol Prog* 24, 907-920 (2008).
31. Davies, P. F. Flow-mediated endothelial mechanotransduction. *Physiological Reviews* 75, 519-560 (1995).
32. Dewey, C. F., Bussolari, S. R., Gimbrone, M. A. & Davies, P. F. The dynamic response of vascular endothelial cells to fluid shear stress. *J. Biomech. Eng.—Trans. ASME* 103, 177-185 (1981).

33. Born, C., Zhang, Z., Alrubeai, M. & Thomas, C. R. Estimation of disruption of animal-cells by laminar shear-stress. *Biotechnology and Bioengineering* 40, 1004-1010 (1992).
34. Nair, K. et al. Characterization of cell viability during bioprinting processes. *Biotechnology Journal* 4, 1168-1177 (2009).
35. Saunders, R. E., Gough, J. E. & Derby, B. Delivery of human fibroblast cells by piezoelectric drop-on-demand inkjet printing. *Biomaterials* 29, 193-203 (2008).
36. Lee, W. et al. On-demand three-dimensional freeform fabrication of multilayered hydrogel scaffold with fluidic channels. *Biotechnology and Bioengineering* 105, 1178-1186 (2010).
37. Pregibon, D. C., Toner, M. & Doyle, P. S. Multifunctional encoded particles for high-throughput biomolecule analysis. *Science* 315, 1393-1396 (2007).
38. Chapin, S. C., Pregibon, D. C. & Doyle, P. S. High-throughput flow alignment of barcoded hydrogel microparticles. *Lab on a Chip* 9, 3100-3109 (2009).
39. Lee, H., Kim, J., Kim, H. & Kwon, S. Colour-barcoded magnetic microparticles for multiplexed bioassays. *Nature Materials* 9, 745-749 (2010).
40. Carrier, R. L. et al. Control of the structure and metabolism of engineered cardiac muscle by direct perfusion of culture medium. *Abstracts of Papers American Chemical Society* 219, 76 (2000).
41. Carrier, R. L. et al. Perfusion improves tissue architecture of engineered cardiac muscle. *Tissue Engineering* 8, 175-188 (2002).
42. Casey, T. M. & Arthur, P. G. Hibernation in noncontracting mammalian cardiomyocytes. *Circulation* 102, 3124-3129 (2000).
43. Iyer, R. K., Chui, J. & Radisic, M. Spatiotemporal tracking of cells in tissue-engineered cardiac organoids. *Journal of Tissue Engineering and Regenerative Medicine* 3, 196-207 (2009).
44. Unger, M. A., Chou, H. P., Thorsen, T., Scherer, A. & Quake, S. R. Monolithic microfabricated valves and pumps by multilayer soft lithography. *Science* 288, 113-116 (2000).
45. Dewey, C. F., Bussolari, S. R., Gimbrone, M. A. & Davies, P. F. THE DYNAMIC-RESPONSE OF VASCULAR ENDOTHELIAL-CELLS TO FLUID SHEAR-STRESS. *Journal of Biomechanical Engineering—Transactions of the Asme* 103, 177-185 (1981).
46. Davies, P. F. FLOW-MEDIATED ENDOTHELIAL MECHANOTRANSDUCTION. *Physiological Reviews* 75, 519-560 (1995).
47. Young, E. W. K., Wheeler, A. R. & Simmons, C. A. Matrix-dependent adhesion of vascular and valvular endothelial cells in microfluidic channels. *Lab on a Chip* 7, 1759-1766 (2007).
48. Plouffe, B. D., Brown, M. A., Iyer, R. K., Radisic, M. & Murthy, S. K. Controlled capture and release of cardiac fibroblasts using peptide-functionalized alginate gels in microfluidic channels. *Lab on a Chip* 9, 1507-1510 (2009).
49. Li, X., et al. Culture of neural stem cells in calcium alginate beads. *Biotechnology Progress* 22, 1683-1689 (2006).
50 7. Kang, E., et al. Digitally tunable physicochemical coding of material composition and topography in continuous microfibres. *Nat Mater* advance online publication (2011).
51 8. Iyer, R. K., Chui, J. & Radisic, M. Spatiotemporal tracking of cells in tissue-engineered cardiac organoids. *Journal of Tissue Engineering and Regenerative Medicine* 3, 196-207 (2009).
52 9. Bird, R. B., Stewart, W. E. & Lightfoot, E. N. *Transport Phenomena*, (Wiley, New York, 2007).

Therefore what is claimed is:

1. A microfluidic device comprising:
   a planar array of microfluidic polymer solution delivery channels, wherein inlets of said polymer solution delivery microfluidic channels are connectable to one or more liquid polymer dispensing devices for delivering polymer solution at a controlled rate;
   a central planar channel having an inlet in fluid communication with outlets of said polymer solution delivery microfluidic channels;
   a first flow focusing microfluidic channel having an inlet connectable to a source of flow focusing liquid and an outlet in fluid communication with a first flow focusing planar channel; and
   a second flow focusing microfluidic channel having an inlet connectable to said source of flow focusing liquid and an outlet in fluid communication with a second flow focusing planar channel;
   wherein said first flow focusing planar channel and said second flow focusing planar channel are respectively located above and below said central planar channel and are in fluid communication with said central planar channel, such that a planar liquid sheet of polymer solution emerging in said central planar channel is contacted, and focused, by planar flows of flow focusing liquid in said first and second flow focusing planar channels in a sandwiched configuration; and
   a polymerization reservoir in fluid communication with the outlet of the planar channel for receiving the planar liquid sheet into an additional liquid for solidification therein.

2. The microfluidic device according to claim 1, wherein inlets of two or more of said polymer solution delivery microfluidic channels are connectable to a common liquid polymer dispensing device for delivering a common polymer solution at a controlled rate.

3. The microfluidic device according to claim 2, wherein inlets of each of said polymer solution delivery microfluidic channels are connectable to a common liquid polymer dispensing device for delivering a common polymer solution to the array of polymer solution delivery microfluidic channels at a controlled rate.

4. The microfluidic device according to claim 2, wherein said array comprises:
   a first set of polymer solution delivery microfluidic channels, wherein an inlet of each first polymer solution delivery microfluidic channel is connectable to a first liquid polymer dispensing device for delivering a base polymer solution at a controlled rate; and
   a second set of second polymer solution delivery microfluidic channels, wherein inlets of said second polymer solution delivery microfluidic channels are connectable to one or more second liquid polymer dispensing device for delivering at least one secondary polymer solution at a controlled rate.

5. The microfluidic device according to claim 4, wherein:
   said first set of first polymer solution delivery microfluidic channels forms a first array of said first polymer solution delivery microfluidic channels;

said second set of second polymer solution delivery microfluidic channels forms a second array of said second polymer solution delivery microfluidic channels; and wherein outlets of said second array of said second polymer solution delivery microfluidic channels are interleaved in between outlets of said first array of said first polymer solution delivery microfluidic channels within a common plane at said inlet of said planar channel.

6. The microfluidic device according to claim 1 further comprising at least one polymer liquid dispensing device in fluid communication with at least one of said polymer solution delivery microfluidic channels for controlling a flow rate of polymer solution within said at least one polymer solution delivery microfluidic channel.

7. The microfluidic device according to claim 6 wherein said at least one polymer liquid dispensing device comprises two or more polymer liquid dispensing devices, wherein each of said two or more polymer liquid dispensing devices is in fluid communication with at least one polymer solution delivery microfluidic channel.

8. The microfluidic device according to claim 6 wherein said at least one polymer liquid dispensing device is:
 a single polymer liquid dispensing device that is in fluid communication with each polymer solution delivery microfluidic channel for delivering a common polymer solution to each said polymer solution delivery microfluidic channel; or
 a plurality of polymer liquid dispensing devices, wherein each said polymer liquid dispensing device is in fluid communication with one polymer solution delivery microfluidic channel for controlling a flow rate of polymer solution within said one polymer solution delivery microfluidic channel.

9. The microfluidic device according to claim 6 further comprising one or more polymer reservoirs for housing the polymer solution, wherein each polymer reservoir is connected to one of said polymer liquid dispensing devices.

10. The microfluidic device according to claim 1 wherein said polymer solution delivery microfluidic channels are formed in a distribution layer of said device, and wherein said first flow focusing microfluidic channel and said second flow focusing microfluidic channel are formed in flow focusing layers of said device, such that said distribution layer is sandwiched between said flow focusing layers.

11. The microfluidic device according to claim 1 further comprising a flow focusing liquid dispensing device adapted to controllably dispense the flow focusing liquid into said first flow focusing microfluidic channel and said second flow focusing microfluidic channel.

12. The microfluidic device according to claim 1 further comprising a rotating mechanism configured for collecting the sheet solidified within the reservoir.

13. The microfluidic device according to claim 1 further comprising a polymerization means for polymerizing the sheet within the reservoir.

14. The microfluidic device according to claim 1 wherein the polymer solution delivery microfluidic channels are configured such that their respective flow resistances are substantially uniform.

15. The microfluidic device according to claim 1 wherein said array of polymer solution delivery microfluidic channels is a first array of first polymer solution delivery microfluidic channels, the device further comprising:
 at least one additional planar array of additional polymer solution delivery microfluidic channels, wherein inlets of said additional polymer solution delivery microfluidic channels are connectable to one or more liquid polymer dispensing devices for delivering polymer solution at a controlled rate;
 wherein said inlet of said central planar channel is in fluid communication with outlets of said additional polymer solution delivery microfluidic channels; and
 wherein said additional polymer solution delivery microfluidic channels are positioned to form a second layer of said planar liquid sheet within said central planar channel.

16. A method of forming a planar polymeric material using a microfluidic device, the method comprising:
 providing a microfluidic device according to claim 1;
 controlling the one or more liquid polymer dispensing devices to dispense the polymer solution into the polymer solution delivery microfluidic channels at a controlled rate;
 dispensing the flow focusing liquid into the first flow focusing microfluidic channel and the second flow focusing microfluidic channel at a controlled rate, such that a planar liquid sheet of polymer solution emerging in said central planar channel is contacted on either side thereof, and focused, by planar flows of flow focusing liquid in said first and second flow focusing planar channels in a sandwiched configuration; and
 solidifying the planar liquid sheet within the additional liquid, thereby forming a planar polymeric material.

17. The method according to claim 16 wherein a composition of the polymer solution and a composition of the additional liquid are selected such that solidification of the planar liquid sheet is initiated when the planar liquid sheet emerges from the output of the central planar channel into the additional liquid.

18. The method according to claim 16 wherein the device is configured such that inlets of each of said polymer solution delivery microfluidic channels are connectable to a common liquid polymer dispensing device for delivering a common polymer solution to the array of polymer solution delivery microfluidic channels at a controlled rate;
 wherein the step of controlling the one or more liquid polymer dispensing devices to dispense the polymer solution comprises:
 controlling the common liquid polymer dispensing device to dispense the common polymer solution into the array of polymer solution delivery microfluidic channels at a controlled rate.

19. The method according to claim 16 wherein inlets of two or more of said polymer solution delivery microfluidic channels are connected to a common liquid polymer dispensing device for delivering a common polymer solution at a controlled rate, wherein the step of controlling the one or more liquid polymer dispensing devices to dispense the polymer solution comprises:
 controlling the common liquid polymer dispensing device to dispense the common polymer solution into the two or more polymer solution delivery microfluidic channels at a controlled rate; and
 controlling each additional liquid polymer dispensing device to dispense polymer solution into each remaining polymer solution delivery microfluidic channel at a controlled rate;
 such that the planar polymeric material is formed with a controlled heterogeneity in composition.

20. The method according to claim 16 wherein the array of microfluidic channels comprises:

a first set of polymer solution delivery microfluidic channels, wherein an inlet of each first polymer solution delivery microfluidic channel is connected to a first liquid polymer dispensing device for delivering a first polymer solution at a controlled rate; and a second set of second polymer solution delivery microfluidic channels, wherein each second polymer solution delivery microfluidic channels is connected to a unique second liquid polymer dispensing device for delivering a second polymer solution at a controlled rate;

wherein the step of controlling the one or more liquid polymer dispensing devices to dispense the polymer solution comprises:

controlling the first liquid polymer dispensing device to dispense the first polymer solution into the first set of polymer solution delivery microfluidic channels at a controlled rate; and controlling the second liquid polymer dispensing devices to dispense the second polymer solution into each second polymer solution delivery microfluidic channel of the second set of microfluidic channels at a controlled rate;

such that the planar polymeric material is formed with a controlled heterogeneity in composition.

21. The method according to claim 20 wherein the device is configured such that:

the first set of first polymer solution delivery microfluidic channels forms a first array of said first polymer solution delivery microfluidic channels;

the second set of second polymer solution delivery microfluidic channels forms a second array of said second polymer solution delivery microfluidic channels; and wherein outlets of said second array of said second polymer solution delivery microfluidic channels are interleaved in between outlets of said first array of said first polymer solution delivery microfluidic channels within a common plane at said inlet of said central planar channel;

wherein the step of controlling the one or more liquid polymer dispensing devices to dispense the polymer solution comprises:

controlling the first liquid polymer dispensing device to dispense the first polymer solution into the first array of polymer solution delivery microfluidic channels at a controlled rate; and controlling the second liquid polymer dispensing devices to dispense the second polymer solution into each second polymer solution delivery microfluidic channel of the second array of microfluidic channels at a controlled rate;

such that the planar polymeric material is formed with a controlled heterogeneity in composition.

22. The method according to claim 16 wherein step of solidifying the planar liquid sheet is performed through one of photopolymerization and thermal polymerization.

23. The method according to claim 16 wherein at least one of the polymer solutions comprises a payload.

24. The method according to claim 23 wherein the payload comprises one or more of chromophores and fluorophores, and wherein the polymer solution is dispensed from such that the planar polymeric material comprises encoded information comprises a barcode.

25. The method according to claim 23 wherein the planar polymeric material is edible and wherein the payload comprises a medicament or a flavor compound.

26. The method according to claim 23 wherein the payload comprises one or more cells.

27. The method according to claim 23 wherein the payload is selected from the group consisting of DNA, RNA, biological molecules, proteins, growth factors, cytokines, assay reagents, beads, beads coated with assay reagents, chromophores, fluorophores, tissues, pieces of tissues and organs.

28. The method according to claim 16 wherein a thickness of the planar polymeric material is between approximately 100 microns and 700 microns, and wherein a width of said planar polymeric material is between approximately 1 mm and 3 cm.

* * * * *